(12) United States Patent
Barlow et al.

(10) Patent No.: US 10,369,318 B2
(45) Date of Patent: Aug. 6, 2019

(54) UNOBTRUSIVE NASAL MASK

(71) Applicant: ResMed Limited, Bella Vista, New South Wales (AU)

(72) Inventors: Adam Francis Barlow, Sydney (AU); Kai Stuebiger, Sydney (AU); Muditha Pradeep Dantanarayana, Sydney (AU); Aaron Samuel Davidson, Sydney (AU); Phoebe Katherine Hill, Sydney (AU); Jessica Lea Dunn, Sydney (AU); Anthony Paul Barbara, Sydney (AU); Jose Ignacio Romagnoli, Sydney (AU); Lochlan Von Moger, Sydney (AU); Kirrily Michele Haskard, Sydney (AU); Justin John Formica, Sydney (AU); Rupert Christian Scheiner, Sydney (AU)

(73) Assignee: ResMed Pty Ltd, Bella Vista (AU)

(*) Notice: Subject to any disclaimer, the term of this patent is extended or adjusted under 35 U.S.C. 154(b) by 295 days.

(21) Appl. No.: 15/299,153

(22) Filed: Oct. 20, 2016

(65) Prior Publication Data

US 2017/0080173 A1 Mar. 23, 2017

Related U.S. Application Data

(62) Division of application No. 13/878,317, filed as application No. PCT/AU2011/001289 on Oct. 7, 2011, now Pat. No. 9,517,320.

(Continued)

(51) Int. Cl.
*A61M 16/06* (2006.01)
*A61M 16/00* (2006.01)
*A61M 16/08* (2006.01)

(52) U.S. Cl.
CPC .... *A61M 16/0683* (2013.01); *A61M 16/0057* (2013.01); *A61M 16/0605* (2014.02);
(Continued)

(58) Field of Classification Search
CPC .......... A41D 13/1146; A61M 16/0057; A61M 16/06; A61M 16/0605; A61M 16/0611;
(Continued)

(56) References Cited

U.S. PATENT DOCUMENTS 2,465,536 A 3/1949 Hyman
2,498,685 A 2/1950 Hyman
(Continued)

FOREIGN PATENT DOCUMENTS

EP 2000168 A1 12/2008
EP 2022528 B1 2/2009
(Continued)

OTHER PUBLICATIONS

First Examination Report dated Sep. 14, 2017 issued in Australian Application No. 2015242960 (5 pages).
(Continued)

*Primary Examiner* — Annette Dixon
(74) *Attorney, Agent, or Firm* — Nixon & Vanderhye P.C.

(57) ABSTRACT

A patient interface for delivering breathable gas to a patient includes a mask having a sealing portion adapted to form a seal with the patient headgear adapted to secure the mask to a head of the patient and an adjustable strap assembly including a pair of straps connected to one another in a length adjustable manner.

22 Claims, 33 Drawing Sheets

Related U.S. Application Data

(60) Provisional application No. 61/391,497, filed on Oct. 8, 2010, provisional application No. 61/422,017, filed on Dec. 10, 2010.

(52) U.S. Cl.
CPC ... *A61M 16/0816* (2013.01); *A61M 2205/582* (2013.01); *A61M 2205/583* (2013.01); *A61M 2210/0618* (2013.01)

(58) Field of Classification Search
CPC .......... A61M 16/0616; A61M 16/0655; A61M 16/0666; A61M 16/0683; A61M 16/0825; A61M 16/1045; A61M 2205/582; A61M 2205/583; A61M 2210/0618; A62B 18/084
See application file for complete search history.

(56) References Cited

U.S. PATENT DOCUMENTS

| | | | |
|---|---|---|---|
| 3,457,564 A | 7/1969 | Holloway | |
| 4,112,521 A | 9/1978 | Uke | |
| 4,196,728 A * | 4/1980 | Granite | A61M 16/1045 128/201.13 |
| 4,463,455 A | 8/1984 | Kirk | |
| 4,607,398 A | 8/1986 | Faulconer | |
| 4,848,334 A | 7/1989 | Bellm | |
| 4,941,236 A | 7/1990 | Sherman | |
| 5,555,571 A | 9/1996 | McCaffrey | |
| 5,983,406 A | 11/1999 | Meyerrose | |
| 6,119,694 A * | 9/2000 | Correa | A61M 16/0666 128/207.13 |
| 6,192,886 B1 * | 2/2001 | Rudolph | A61M 16/06 128/205.25 |
| 7,523,754 B2 | 4/2009 | Lithgow et al. | |
| 7,546,837 B2 * | 6/2009 | Busch | A61M 16/06 128/206.21 |
| 8,474,458 B1 * | 7/2013 | Yadven | A61M 16/0683 128/200.24 |
| 8,826,909 B2 * | 9/2014 | Nashed | A61M 16/06 128/200.24 |
| 2002/0117177 A1 * | 8/2002 | Kwok | A61M 16/06 128/207.11 |
| 2002/0129439 A1 | 9/2002 | Kawakita | |
| 2003/0145859 A1 * | 8/2003 | Bohn | A61M 16/06 128/206.24 |
| 2005/0076913 A1 * | 4/2005 | Ho | A61M 16/06 128/206.27 |
| 2005/0155604 A1 | 7/2005 | Ging et al. | |
| 2005/0199246 A1 | 9/2005 | Frank | |
| 2006/0032504 A1 * | 2/2006 | Burton | A61M 16/06 128/207.11 |
| 2006/0060200 A1 | 3/2006 | Ho et al. | |
| 2006/0081252 A1 | 4/2006 | Wood | |
| 2006/0196511 A1 * | 9/2006 | Lau | A61M 16/0666 128/207.11 |
| 2006/0272645 A1 | 12/2006 | Ging et al. | |
| 2007/0044803 A1 * | 3/2007 | Xue | A41D 13/1146 128/206.21 |
| 2007/0144525 A1 | 6/2007 | Davidson et al. | |
| 2007/0235033 A1 * | 10/2007 | Reier | A62B 18/084 128/207.11 |
| 2007/0245467 A1 | 10/2007 | Lilenthal et al. | |
| 2008/0066759 A1 | 3/2008 | Howard et al. | |
| 2008/0083412 A1 * | 4/2008 | Henry | A61M 16/0683 128/207.11 |
| 2008/0178875 A1 | 7/2008 | Henry | |
| 2008/0245369 A1 | 10/2008 | Matula et al. | |
| 2009/0032024 A1 * | 2/2009 | Burz | A61M 16/06 128/206.24 |
| 2009/0044808 A1 * | 2/2009 | Guney | A61M 16/0666 128/206.24 |
| 2010/0229868 A1 | 9/2010 | Rummery et al. | |
| 2011/0220115 A1 * | 9/2011 | Castiglione | A62B 18/084 128/206.27 |
| 2013/0220327 A1 | 8/2013 | Barlow et al. | |
| 2015/0250972 A1 * | 9/2015 | Haibach | A61M 16/0683 128/202.27 |

FOREIGN PATENT DOCUMENTS

| | | |
|---|---|---|
| WO | 01/97893 A1 | 12/2001 |
| WO | 2004/041342 A1 | 5/2004 |
| WO | 2006/096924 A1 | 9/2006 |
| WO | 2007/053878 A1 | 5/2007 |
| WO | 2009/052560 A1 | 4/2009 |
| WO | 2010/066004 | 6/2010 |
| WO | 2010/139014 A1 | 12/2010 |

OTHER PUBLICATIONS

Patent Examination Report No. 2 dated Apr. 23, 2015 in Australian Application No. 2011313825 (6 pages).
Third Examination Report dated Jun. 18, 2015 issued in Australian Application No. 2011313825 (3 pages).
Extended European Search Report dated Jun. 18, 2015 issued in European Application No. 11830128.2 (7 pages).
Communication Pursuant to Rules 70(2) and 70a(2) dated Jul. 7, 2015 issued in European Application No. 11830128.2 (1 page).
International Search Report for corresponding PCT Application No. PCT/AU2011/001289 filed Oct. 7, 2011, dated Feb. 15, 2012, 6 pages.
Von Moger et al., U.S. Appl. No. 61/391,497, filed Oct. 8, 2010.
Barlow et al., U.S. Appl. No. 61/422,017, filed Dec. 10, 2010.
First Examination Report dated Oct. 11, 2013 in New Zealand Application No. 609162 (2 pages).
Further Examination Report dated Dec. 17, 2014 in New Zealand Application No. 609162 (2 pages).
Extended European Search Report dated Mar. 20, 2019 issued in European Application No. 18188808.2 (9 pages).

* cited by examiner

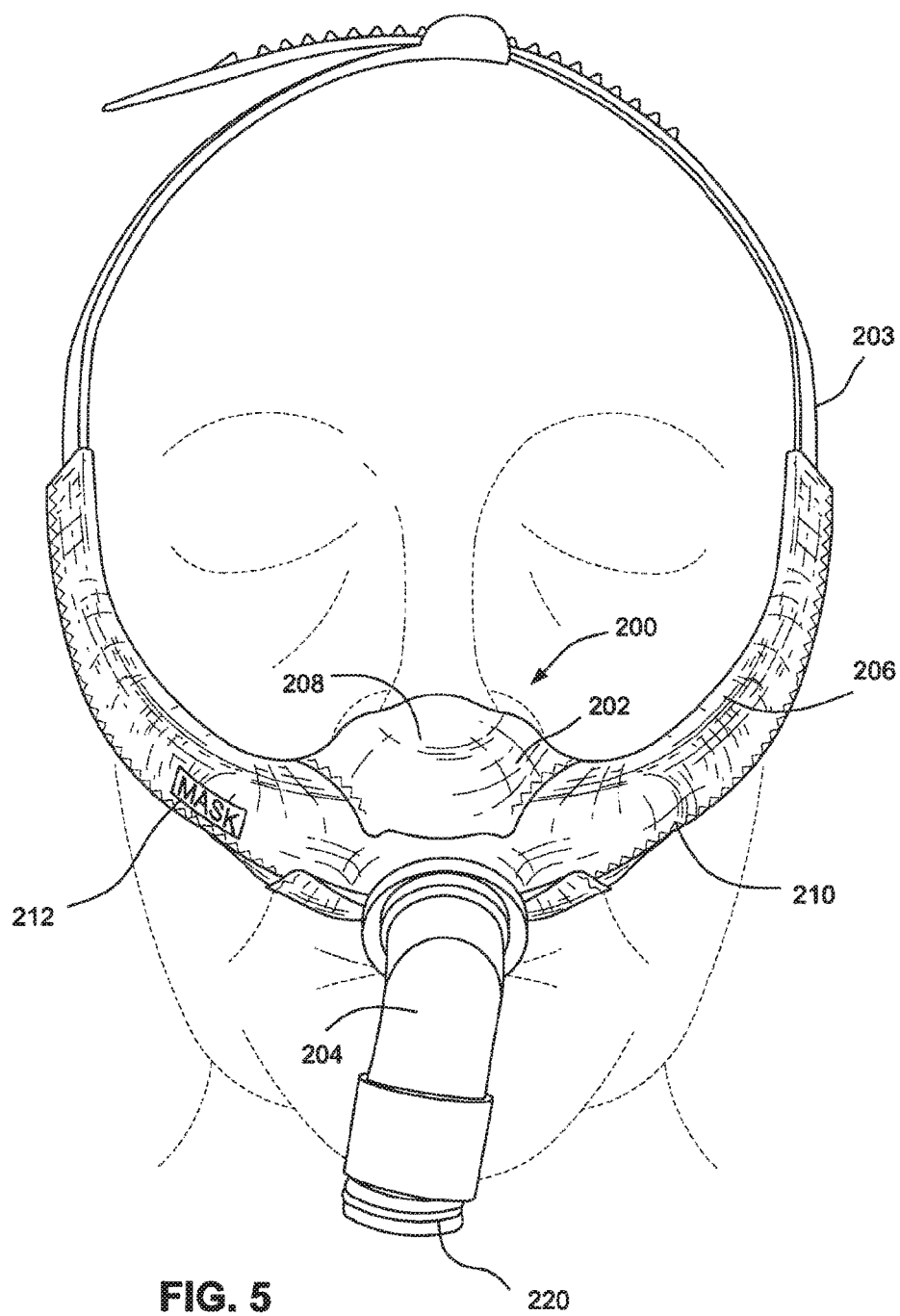

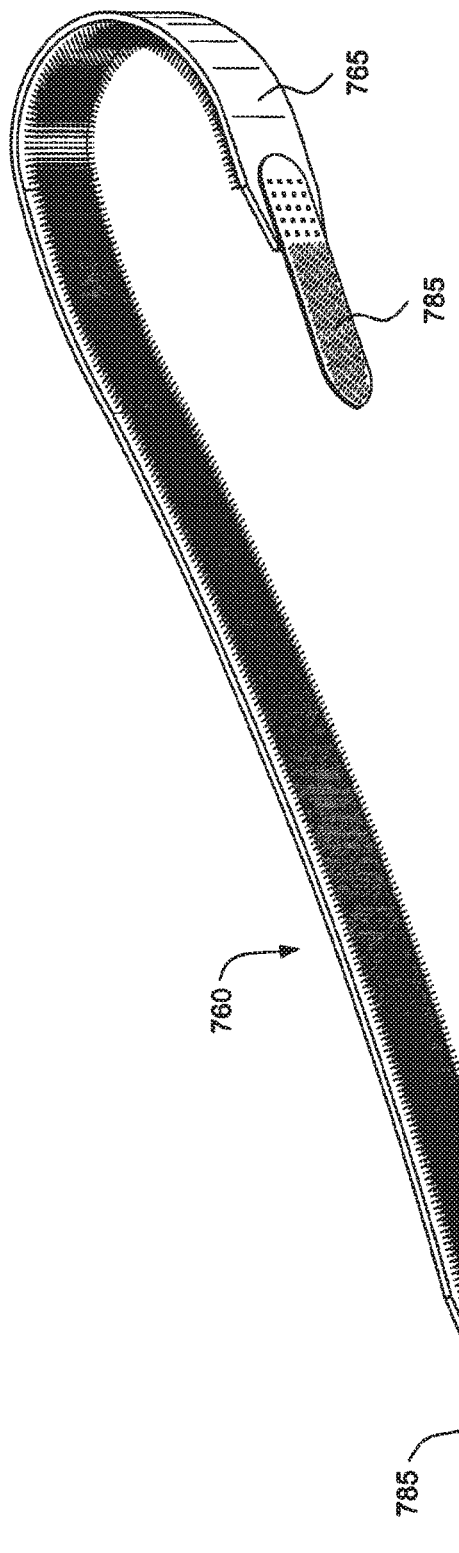
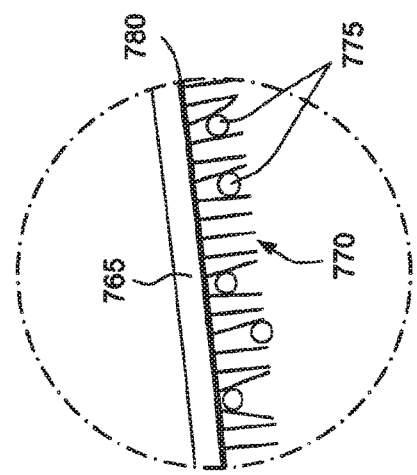
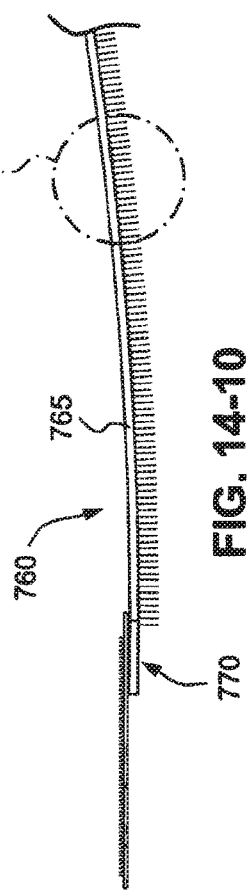
FIG. 14-9
FIG. 14-10
FIG. 14-11

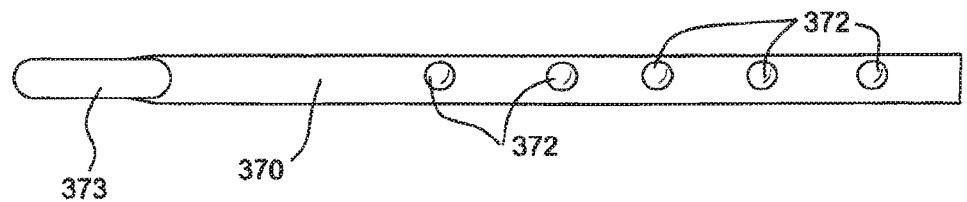
FIG. 15
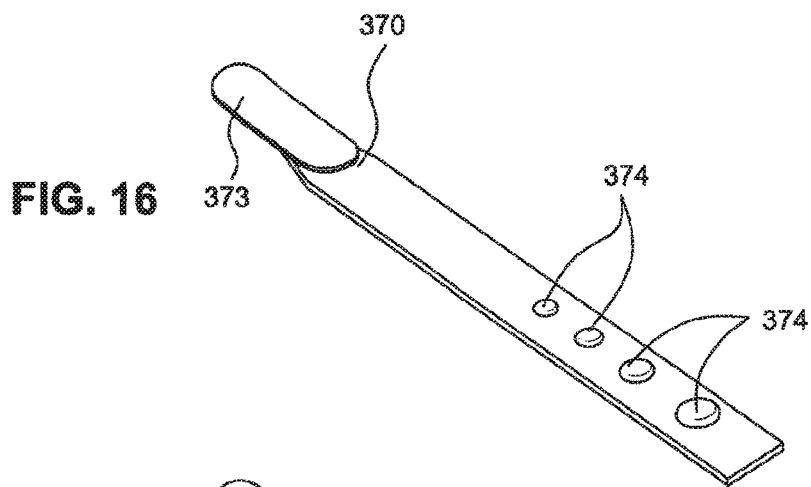
FIG. 16
FIG. 17
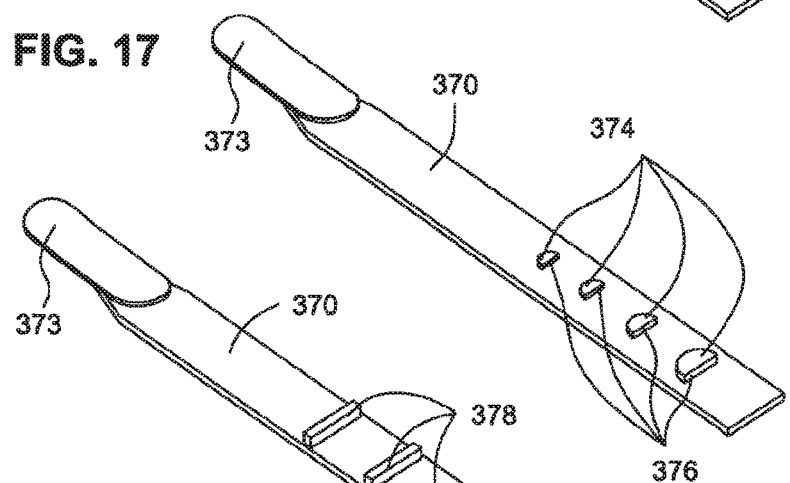
FIG. 18
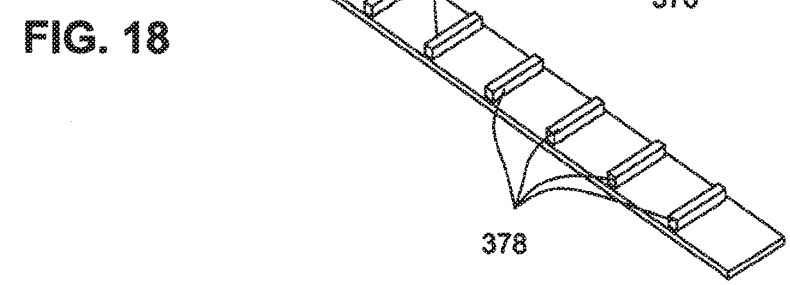

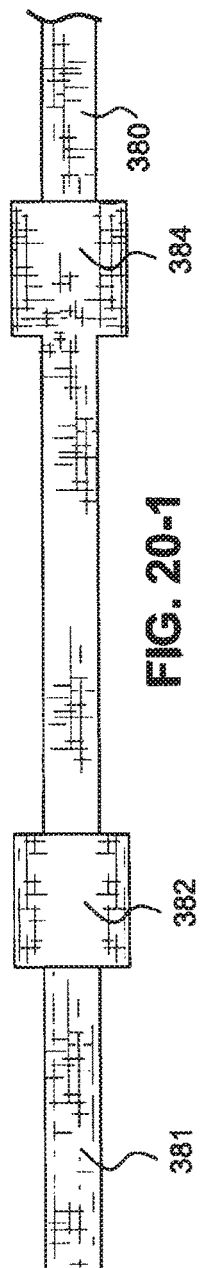
FIG. 20-1
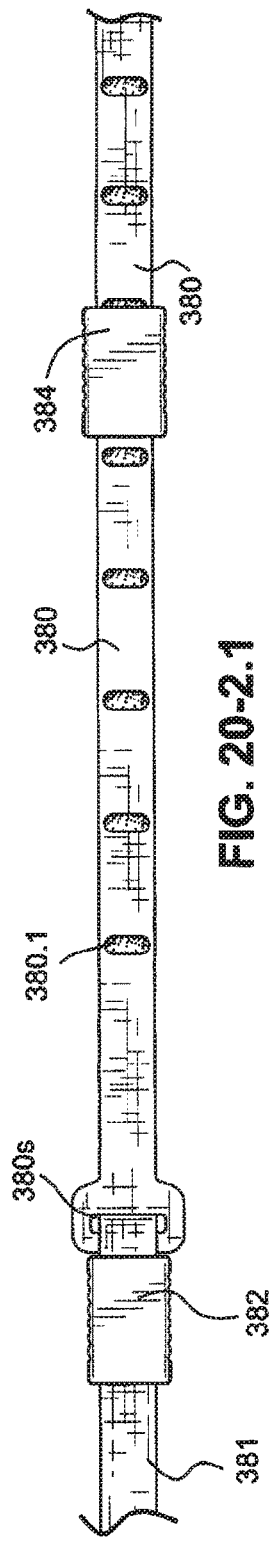
FIG. 20-2.1
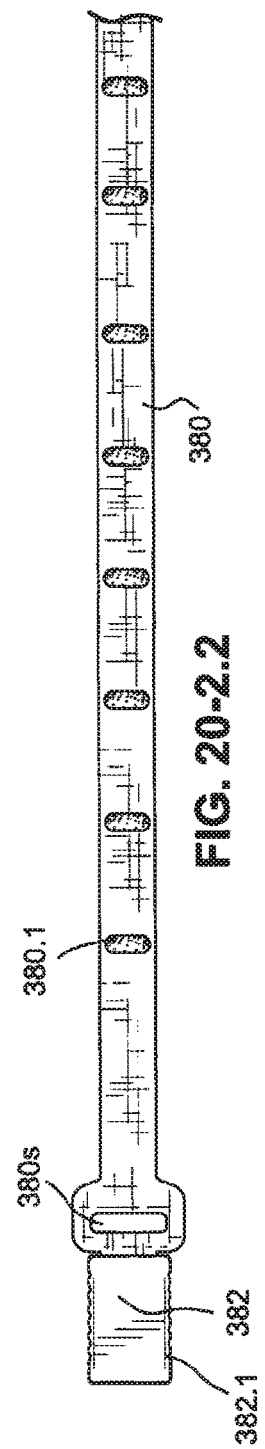
FIG. 20-2.2
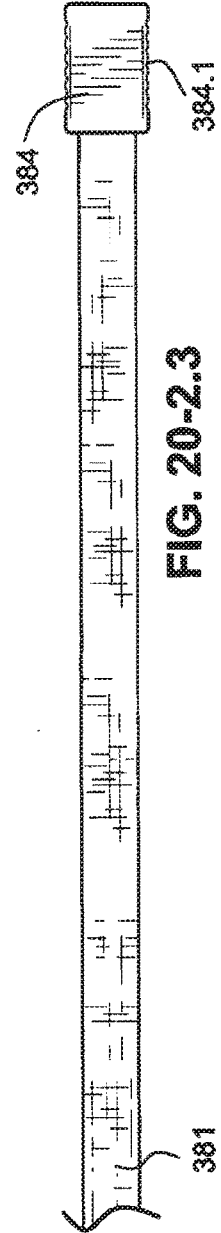
FIG. 20-2.3

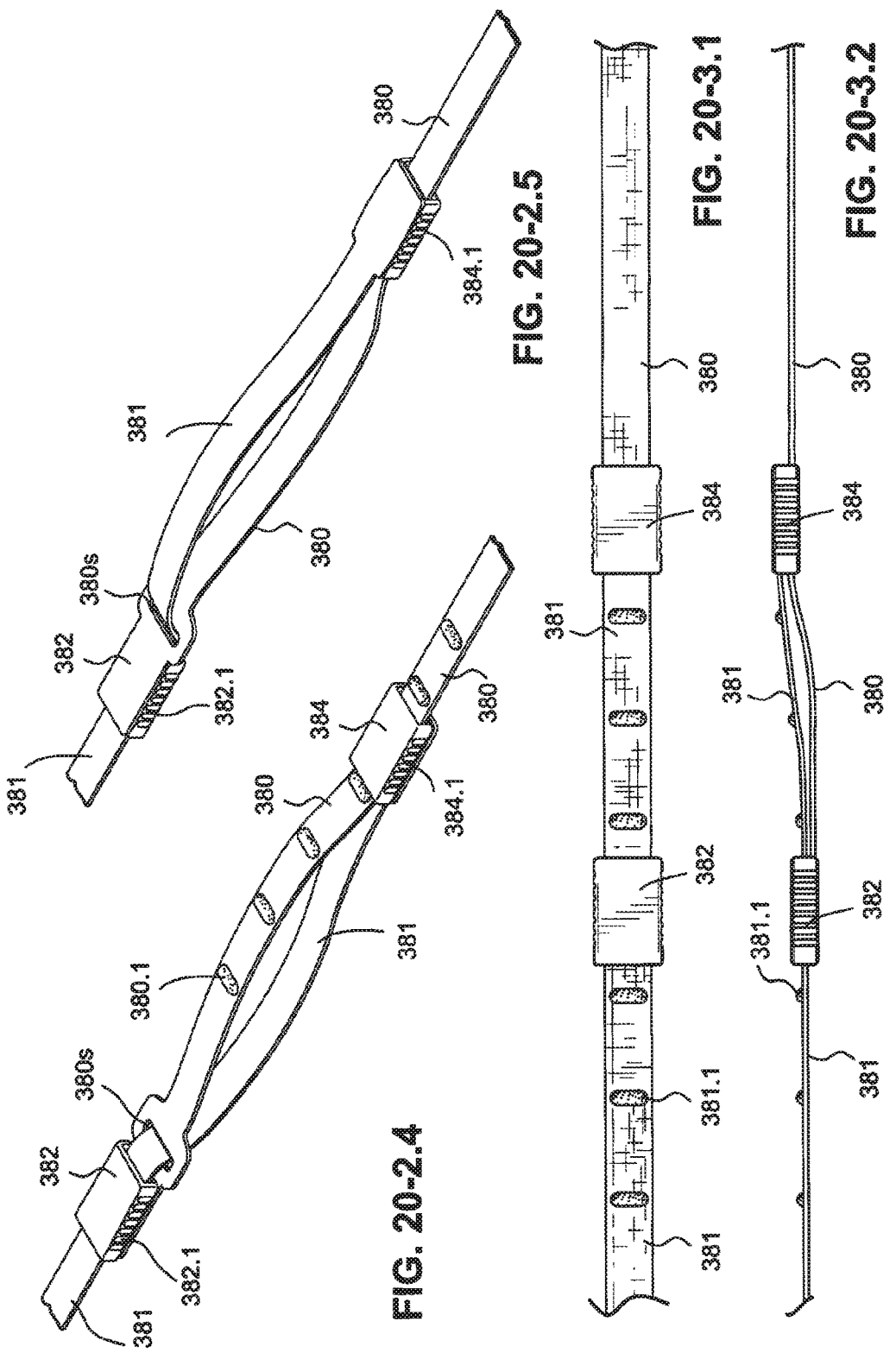

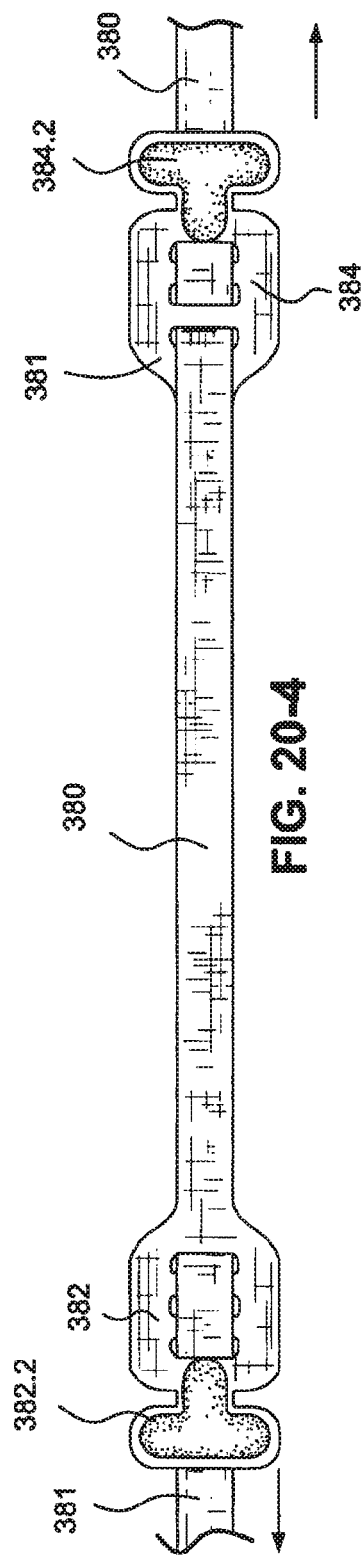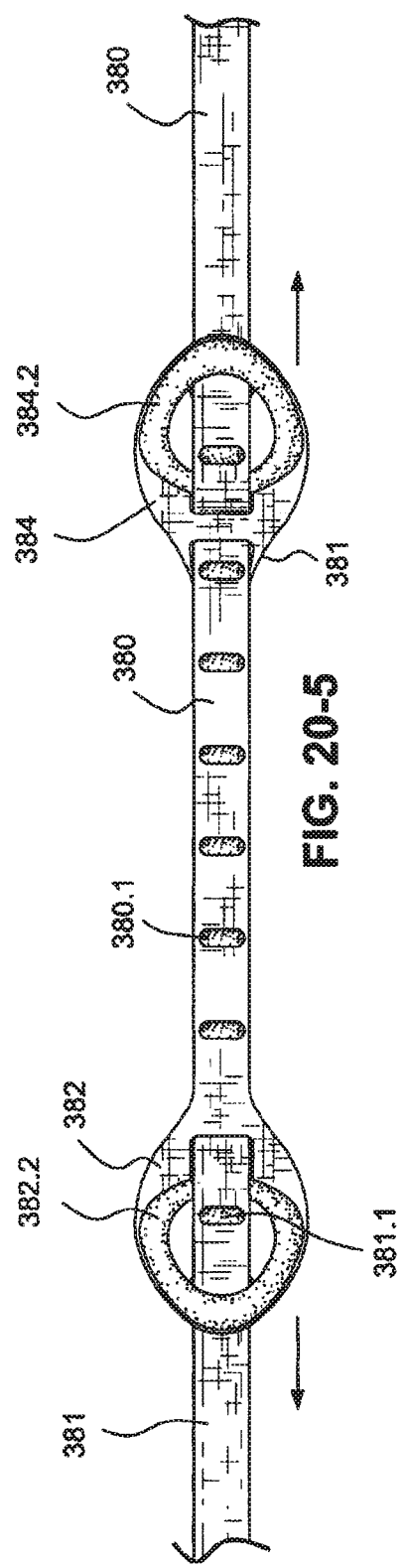
FIG. 20-4
FIG. 20-5

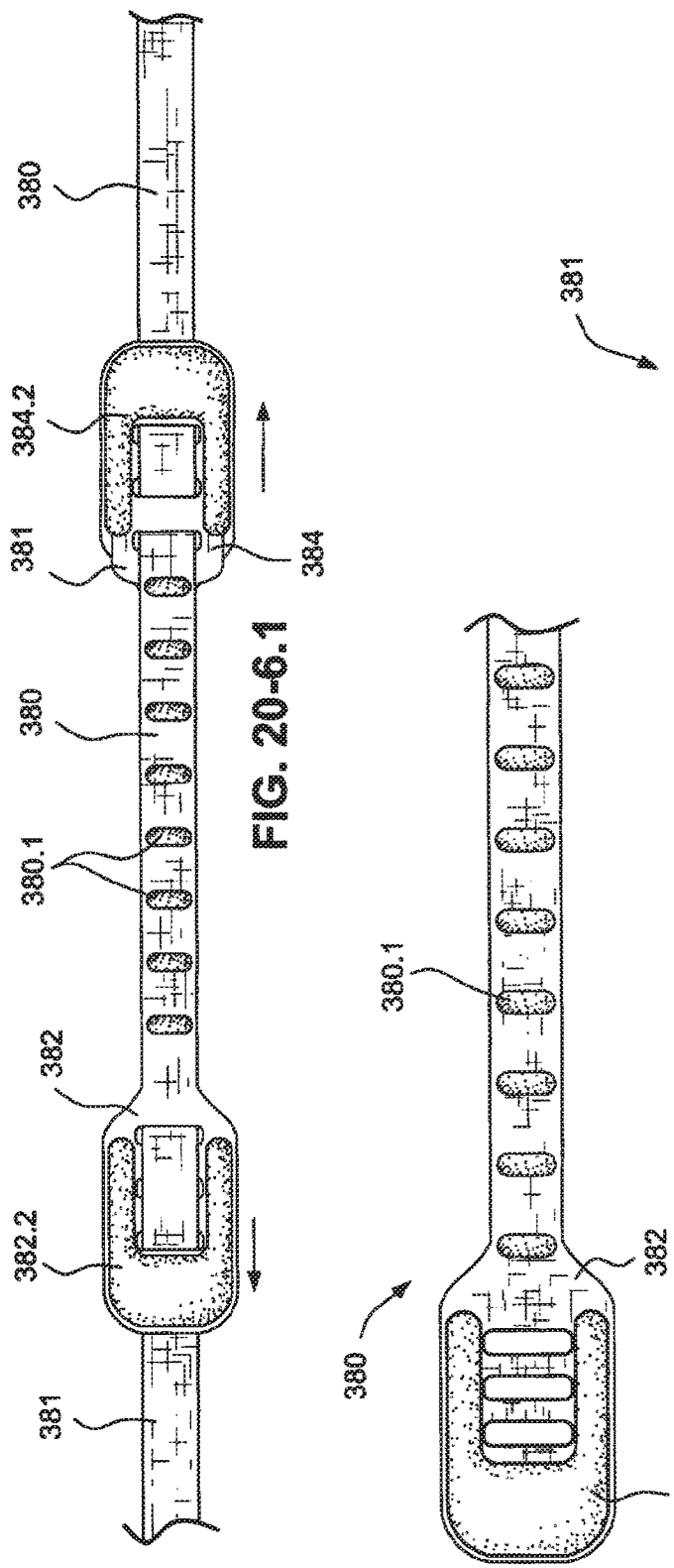
FIG. 20-6.1
FIG. 20-6.2
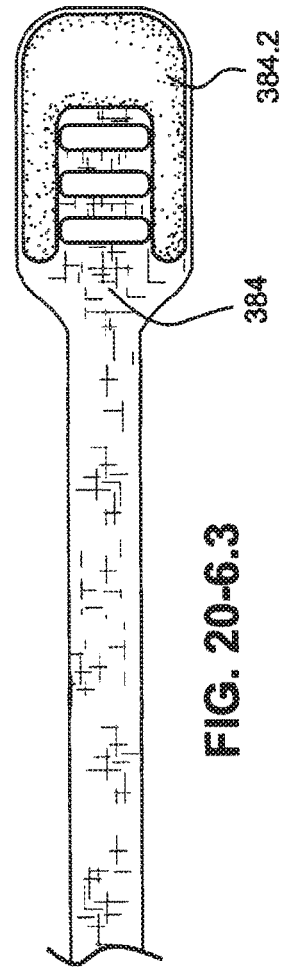
FIG. 20-6.3

UNOBTRUSIVE NASAL MASK

CROSS-REFERENCE TO APPLICATIONS

This application is a divisional of U.S. application Ser. No. 13/878,317, filed Apr. 9, 2013, which is the U.S. national phase of International Application No. PCT/AU2011/001289 filed 7 Oct. 2011 which designated the U.S. and claims priority to U.S. Provisional Application Nos. 61/391,497 filed 8 Oct. 2010 and 61/422,017 filed 10 Dec. 2010, the entire contents of each of which are hereby incorporated by reference.

FIELD OF THE INVENTION

The technology relates to a respiratory mask or patient interface for use with an air delivery system for treatment, e.g., of Sleep Disordered Breathing (SDB) with Continuous Positive Airway Pressure (CPAP) or Non-Invasive Positive Pressure Ventilation (NIPPV). In particular, the technology relates to a respiratory mask that is unobtrusive.

BACKGROUND OF THE INVENTION

Apparatus to deliver breathable gas to a patient typically includes a positive airway pressure (PAP) device, an air delivery conduit or tube, and a patient interface, wherein the patient interface contacts the patient's face in use to deliver pressurized breathable gas to the patient from the PAP device.

In use, the patient interface can appear bulky and as such may discourage patients from using treatment as it is too obtrusive. This in turn may lead to lower therapy compliance and thus failed treatment.

Patients using nasal pillows or puffs may dislike the placement of the pillows in the nares and/or the sensation of pressurized air being directed up the nares (also known as the 'air jetting' affect).

Therefore, a need has developed in the art to provide alternative patient interfaces that are less obtrusive, may not include placement of pillows up the nares and/or may reduce the sensation of pressurized air being directed in the nares.

SUMMARY OF THE INVENTION

One aspect of the present technology relates to a patient interface for delivering breathable gas to a patient. Another aspect of the present technology is a patient interface that forms a seal on an underside of a patient's nose. Another aspect of the present technology is a patient interface that avoids contact with a nasal bridge region of a patient's nose. Another aspect of the present technology is a patient interface that forms a seal on an underside of a patient's nose in a region surrounding both nares. Another aspect of the present technology is a patient interface that avoids contacting the nasal septum. Another aspect of the present technology is a patient interface defining a single breathing chamber that provides a supply of air at positive pressure for both nostrils.

In accordance with one form of the present technology, a patient interface having a mask and headgear is provided that includes an alignment indicator on the mask and an alignment indicator on the headgear so that the headgear may be correctly aligned with the mask.

Another aspect of the present technology is a size indicator disposed on the mask. Another aspect of the present technology is a brand indicator disposed on the mask. Another aspect of the present technology is an orientation indicator disposed on the mask.

Another aspect of the present technology is a patient interface having a mask and headgear, the patient interface including a facial pad on the mask.

Another aspect of the present technology is a patient interface having a mask and headgear, the patient interface including a facial pad on the mask and on at least a portion of the headgear. The pad or wrap may include certain portions designed for flexibility and others designed for relatively more stiffness. Pad/wrap may include wrapping portions that can be opened to allow positioning and receipt of the headgear, and then closed (via hook and loop fastener) to secure the headgear/mask in place.

Another aspect of the present technology is a patient interface having a mask and headgear, the headgear having first and second separable strap portions, with alignment indicators on the mask, on the first strap portion and on the second strap portion.

Another aspect of the present technology is a patient interface having a mask and headgear, with adjustment indicators on the headgear adapted to indicated a degree of adjustment of the headgear.

Another aspect of the present technology is a patient interface having a mask and headgear, the headgear having first and second ends and headgear cuffs adapted to adjustably connect the first and second ends of the headgear.

Another aspect of the present technology is directed to a headgear that can maintain its position on the head. In an example, the headgear may be mechanically coupled to the patient's hair, whilst not being too sticky or pulling on the hair.

Another aspect of the present technology is a patient interface having a mask and headgear, the mask having at least one adjustment device to selectively adjust a position (e.g., length and/or tightness) of the headgear, the height of a forehead support; and/or the angle of tilt of the mask relative to the patient's face, e.g., by providing straps connected along a portion of their length and movable (e.g., slidable) relative to one another.

Another aspect of the present technology is a patient interface having a mask and headgear, the mask having headgear clips/connectors with selectively adjustable positions adapted to selectively loosen or tighten the headgear.

Another aspect of the invention relates to a method for forming headgear. One such method includes forming a laminate with a stiffener/ridigizer (e.g., plastic, metal, etc.). A portion of the laminate, e.g., a fabric portion, may be removed from the stiffener, to expose it in on or more regions.

Another aspect of the present technology is a patient interface for delivering breathable gas to a patient, the patient interface including a mask having a sealing portion adapted to form a seal with the patient's nares, the sealing portion having a supporting wall defining an air path, the sealing portion being structured to extend or curve outwardly from a supporting wall defining an air path, headgear adapted to secure the mask to a head of the patient, a first alignment indicator provided to the mask, and a second alignment indicator provided to the headgear, wherein the first and second alignment indicators are positioned to align with each other when the headgear is connected to the mask with a correct alignment.

Another aspect of the present technology is a patient interface for delivering breathable gas to a patient, the patient interface including a mask having a sealing portion adapted to form a seal with the patient's nares, the sealing portion having a supporting wall defining an air path, headgear adapted to secure the mask to a head of the patient, and a facial pad disposed around the mask, wherein the sealing portion is structured to extend or curve outwardly from a supporting wall defining an air path.

Another aspect of the present technology is a patient interface for delivering breathable gas to a patient, the patient interface including a mask having a sealing portion adapted to form a seal with the patient, the mask having headgear connectors, headgear adapted to secure the mask to a head of the patient, the headgear having a first strap portion and a second strap portion, the first strap portion adapted to connect to the mask, the second strap portion adapted to connect to and be separable from the first strap portion, a first alignment indicator disposed on the mask, a second alignment indicator disposed on the first strap portion, and a third alignment indicator disposed on the second strap portion, wherein the first and second alignment indicators are positioned to align with each other when the first strap portion is connected to the mask with a correct alignment, and the second and third alignment indicators are positioned to align with each other when the first strap portion is connected to the second strap portion with a correct alignment.

Another aspect of the present technology is a patient interface for delivering breathable gas to a patient, the patient interface including a mask having a sealing portion adapted to form a seal with the patient, the mask having headgear connectors each having a slot, and headgear adapted to adjustably connect to the slots of the headgear connectors to secure the mask to a head of the patient, the headgear having a plurality of spaced adjustment indicators, the spaced adjustment indicators positioned on the headgear to be selectively pulled through the slots as the headgear is tightened, wherein a degree of tightness is indicated by a number of the adjustment indicators pulled through the slots.

Another aspect of the present technology is a patient interface for delivering breathable gas to a patient, the patient interface including a mask having a sealing portion adapted to form a seal with the patient, headgear adapted to adjustably connect the mask to a head of the patient the headgear including a first headgear strap and a second headgear strap, a first headgear cuff provided on an end portion of the first headgear strap, the first headgear cuff including a first pair of wing portions and a first tab, and a second headgear cuff provided on an end portion of the second headgear strap, the second headgear cuff including a second pair of wing portions and a second tab, wherein the first headgear strap is adapted to adjustably connect to the second headgear strap by connecting the first pair of wing portions of the first headgear cuff around the second headgear strap and connecting the second pair of wing portions of the second headgear cuff around the first headgear strap.

Another aspect of the present technology is a patient interface for delivering breathable gas to a patient, the patient interface including a mask having a sealing portion adapted to form a seal with the patient, a first headgear chord connected to a first side of the mask, a second headgear chord connected to a second side of the mask, headgear adapted to connect to the first and second headgear chords to secure the mask to a head of the patient, and at least one adjustment device on the mask adapted to selectively move the first and second headgear chords to tighten or loosen the headgear.

Another aspect of the present technology is a patient interface for delivering breathable gas to a patient, the patient interface including a mask having a sealing portion adapted to form a seal with the patient, the mask including a first side portion having a first aperture and a second side portion having a second aperture, a first headgear clip adapted to selectively move within the first aperture to one of a plurality of positions, a second headgear clip adapted to selectively move within the second aperture to one of a plurality of positions, and headgear adapted to connect to the first and second headgear clips to secure the mask to a head of the patient, wherein the headgear is selectively adjustably by movement of the first and second headgear clips.

Another aspect of the present technology is a patient interface for delivering breathable gas to a patient, the patient interface including a mask having a sealing portion adapted to form a seal with the patient, headgear adapted to adjustable connect the mask to a head of the patient the headgear including a first headgear strap and a second headgear strap, and wherein the first headgear strap is adjustably connected to the second headgear strap in a first position and the second headgear strap being adjustably connected to the first headgear strap in a second position spaced from the first position.

Another aspect of the present technology is a patient interface including a mask, a first strap and a second strap, wherein the first and second straps are adjustably coupled to one another and/or the mask to tilt the mask in a plurality of positions.

Another aspect of the present technology is a strap arrangement including at least one strap to engage with a patient's head, the at least one strap being made of a material and/or having a structure to maintain the position of the strap relative to the patient's head in use.

Other aspects, features, and advantages of the present technology will become apparent from the following detailed description when taken in conjunction with the accompanying drawings, which are a part of this disclosure and which illustrate, by way of example, principles of this technology.

BRIEF DESCRIPTION OF THE DRAWINGS

The accompanying drawings facilitate an understanding of the various embodiments of this technology. In such drawings:

FIGS. 3-1 and 3-2 are isometric views of a sealing portion of a patient interface according to an embodiment of the present technology;

FIG. 5-1 is a perspective view of a wrap and a portion of a mask and headgear according to an embodiment of the technology;

FIG. 5-2 is a perspective view of the wrap of FIG. 5-1 in isolation without the mask/headgear and in an open position;

FIGS. 6-1 to 6-8 are front views illustrating a patient interface with alignment, sizing, model and/or brand indicators according to embodiments of the present technology;

FIG. 7 is a front perspective view of a patient interface with an orientation indicator on a model patient according to an embodiment of the present technology;

FIG. 8 is a side view of the patient interface of FIG. 7 on a model patient;

FIG. 12-1 is a front perspective view of a patient interface with an orientation indicator on the head strap according to an embodiment of the present technology;

FIG. 12-2 is a cross-sectional view through line 12-2, 12-2 of FIG. 12-1;

FIG. 13-1 is a front perspective view of a patient interface with an alignment or orientation indicator according to an embodiment of the present technology;

FIGS. 13-2 and 13-3 are cross-sectional views of the head strap of FIG. 13-1;

FIG. 14-1 is a front perspective view of a patient interface with an alignment or orientation indicator according to an embodiment of the present technology;

FIGS. 14-2, 14-3, 14-4, and 14-5 are cross-sectional views of the back strap of FIGS. 14-1;

FIGS. 14-6 to 14-11 illustrate variants of headgear according to the present technology;

FIG. 15 is a top view of a head strap with adjustment indicators according to an embodiment of the present technology;

FIG. 16 is a perspective view of a head strap with adjustment indicators according to an embodiment of the present technology;

FIG. 17 is a perspective view of a head strap with adjustment indicators according to an embodiment of the present technology;

FIG. 18 is a perspective view of a head strap with adjustment indicators according to an embodiment of the present technology;

FIGS. 20-1 to 20-6.3 illustrate headgear straps according to variants of the present technology;

FIGS. 22-1 to 22-2 show schematic views of a headgear strap formation process according to an embodiment of the present technology;

FIG. 22-3 is a top view of the headgear strap of FIG. 22-2;

FIG. 22-4 shows a schematic view of a headgear strap formation process according to an embodiment of the present technology.

FIGS. 26-1 to 26-3 show a headgear adjustment mechanism according to an embodiment of the present technology;

FIGS. 26-4 to 26-6 illustrate a headgear adjustment mechanism according to a variant of the present technology; and FIGS. 27-1 and 27-2 are schematic partial views showing a headgear connector according to an embodiment of the present technology.

DETAILED DESCRIPTION OF ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the PAP devices or blowers described herein may be designed to pump fluids other than air.

1. PAP System

Figure 1:
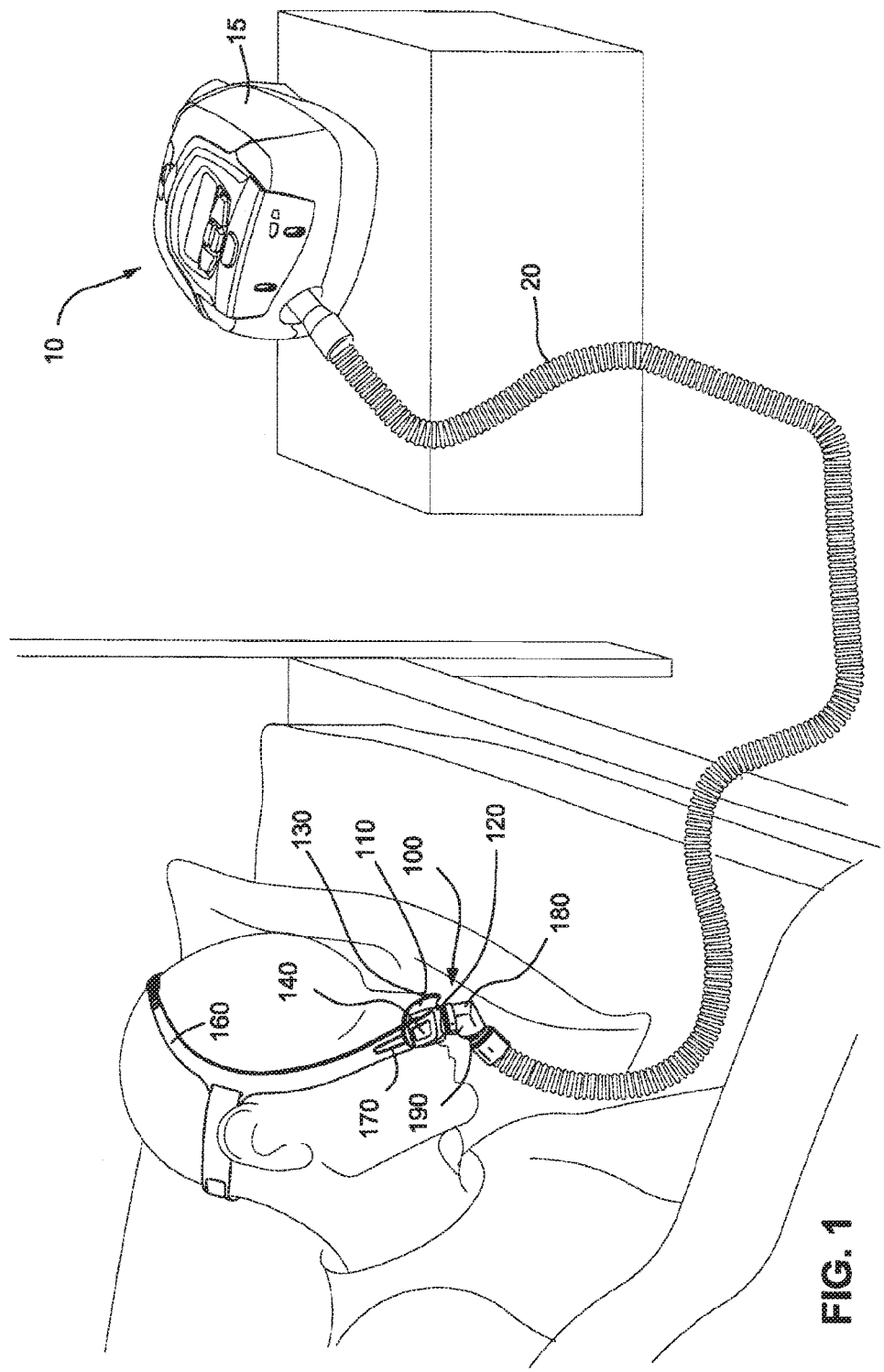
FIG. 1 shows a PAP system with a patient interface according to an embodiment of the technology in use on a patient.

As shown in FIG. 1, a PAP system 10 generally includes a PAP device 15, an air delivery conduit 20 (also referred to as an air delivery tube or tubing), and a patient interface 100. In use, the PAP device 15 generates a supply of pressurized air that is delivered to the patient via the air delivery conduit 20 that includes one end coupled to the outlet of the PAP device 15 and an opposite end coupled to the patient interface 100.

2. Patient Interface

Figure 2:
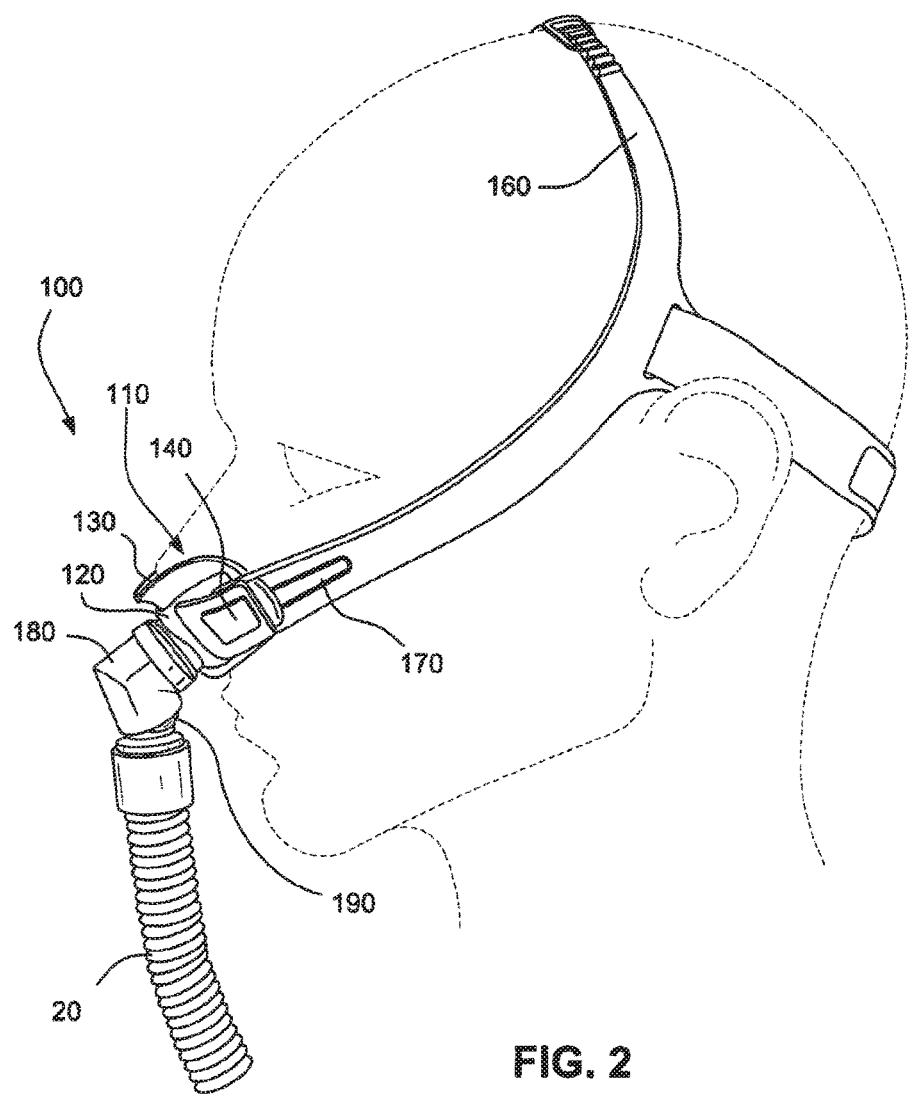
FIG. 2 is a perspective side view of a patient interface with an elbow and supply tube on the patient in use according to an embodiment of the present technology.

The patient interface 100 may include a mask 110 and headgear 160 structured to maintain the mask 110 in position on the patient's face in use, as shown in FIG. 2. The mask 110 may include a sealing portion 130, a supporting portion 120, an elbow 180 (e.g., with swivel) adapted to be connected to the air delivery tube 20, and headgear connectors 140 adapted to connect the mask 110 to headgear 160. A ball and socket connection 190 may be included between the elbow 180 and the air delivery tube 20 allowing additional movement of the air delivery tube 20 without disturbing the seal of the mask 110. The mask 110 comfortably engages the patient's face and provides a seal. The patient interface may include one or more aspects of the patient interface disclosed in PCT/AU2010/000684, filed 9 Jun. 2010, which is incorporated herein by reference in its entirety.

3. Mask

FIGS. 1 and 2 illustrate the mask 110 in use on a model patient's head. The mask 110 illustrated is a nasal mask, although other types of masks could also be used, such as a mouth only mask, a full face mask or nasal prongs. The mask 110 includes the supporting portion 120, and the sealing portion 130, and may additionally include headgear connectors 140 (e.g., slots or clips on the supporting portion adapted to engage headgear straps) adapted to connect to headgear 160.

3.1 Sealing Portion

Sealing portion 130 interfaces with the patient in use, allowing delivery of breathable gas to the patient. In the illustrated embodiment, sealing portion 130 may form a seal with the nares of the patient in use. For example, sealing portion 130 may interface and thus seal with the external portion of each of the alar or nostril flares, the upper lip and/or base of the nares, and the tip of the nose. Sealing portion 130 may be made from materials including but not limited to: silicone, thermoplastic elastomer, gel, foam, or any other suitably conformable material. The material may have a durometer of about 1 to 15 Shore A. Preferably, the material may have a durometer of about 3 to 10 Shore A. Preferably, the material may have a durometer of about 5 to 12 Shore A. Most preferably, the material may have a durometer of about 5 Shore A. Thus, the preferred sealing portion provides a non-invasive arrangement that does not extend into the patient's nostrils in use. The preferred sealing portion 130 does not inflate, and thus does not require inflation pressure to form a seal. Preferably, the seal is not pressure assisted, although it could be modified for such. In one form, the sealing portion 130 could use a gusset (e.g., having a projected area greater than the area of the sealing portion) to help provide a seal as disclosed in U.S. Pat. No. 7,523,754 or WO 01/97893 A1, which are incorporated herein by reference in their entirety.

In an embodiment, the sealing portion 130 may include a wall thickness of about 0.1-15 mm. Preferably, the sealing portion 130 may have a wall thickness of about 2 to 10 mm. Preferably, the sealing portion 130 may have a wall thickness of about 7 to 12 mm. Preferably, the sealing portion 130 may have a wall thickness of about 1-5 mm. Most preferably, the sealing portion 130 may have a wall thickness of about 1-3 mm. Most preferably, the sealing portion 130 may have a wall thickness of about 1.5 mm. The wall thickness may vary in different regions of the sealing portion, e.g., thickness of about 0.5 mm in thinner regions and ranging up to about 2-10 mm in thicker regions. Alternatively, the sealing portion 130 may include a constant wall thickness, e.g., about 1.2 mm. The walls may be constructed of various layers of material, each layer of material having a different hardness and/or thickness (e.g., two layers each being 1.2 mm thick but having different durometer silicones).

The sealing portion 130 may be formed from a material and with a softness to provide patient comfort, and to readily conform to the patient's face. For example, the sealing portion 130 may be a liquid silicone rubber material or another elastomeric material, e.g. TPE. The sealing portion 130 may have a durometer of about 5-40 Shore A (preferably about 5-15 Shore A, most preferably about 5 Shore A) to provide comfort to the patient.

3.1.1 Shape

In the illustrated embodiments, sealing portion 130 (also referred to as a nasal cradle) may have a generally cradle, cup or U shape such that when positioned under the nose of the patient, it is conformed or generally shaped to the alar angle of the patient.

The generally smooth curvature or undulating shape of sealing portion 130 may be comfortable as it can flex to accommodate a variety of nose shapes and sizes. The general shape of sealing portion 130 may also infer comfort and unobtrusiveness to the patient, thereby increasing compliance.

Alternatively, sealing portion 130 may be generally flat yet be able to flex into the desired alar angle of the patient. This may be achieved by providing sealing portion 130 with portions of reduced thickness to encourage bending and/or constructing sealing portion 130 from a flexible material or incorporating portions of flexible material.

3.1.2 Aperture

Figures 1, 3:
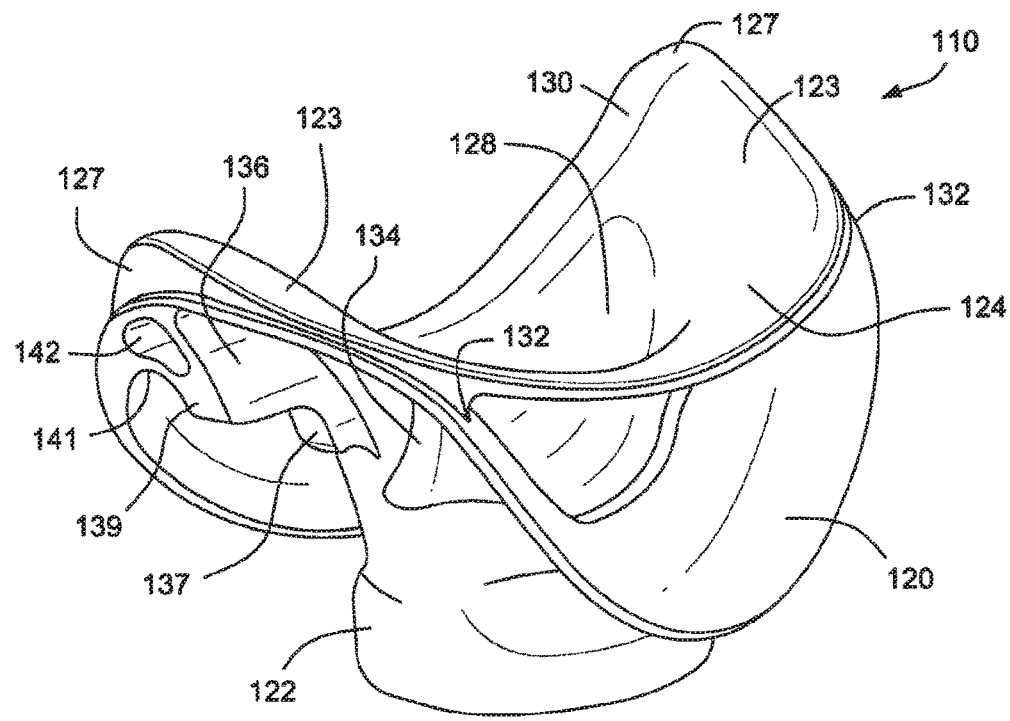
Figures 2, 3:
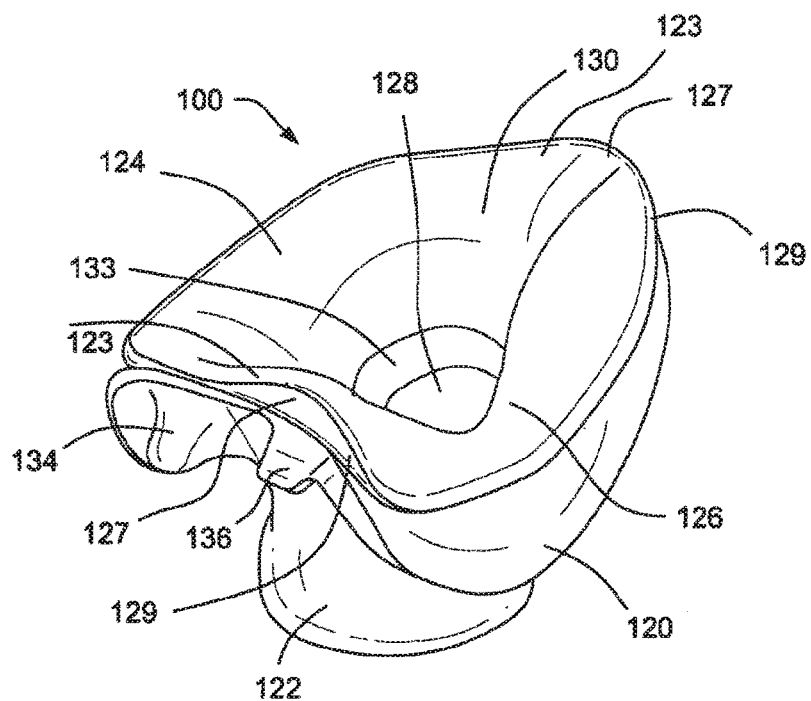

As best shown in FIGS. 3-1 and 3-2, sealing portion 130 may have an aperture 128 that allows the passage of breathable gas from the air delivery conduit 20 to the patient. Aperture 128 may be generally circular, rectangular, or any other desired shape (e.g., trapezoidal or oval shaped). In an embodiment, aperture 128 may be shaped so as to indicate the alignment or orientation of the sealing portion 130 with the patient's nose in use, e.g., trapezoidal or triangular shapes.

The aperture 128 of the sealing portion 130 may be larger when compared to that of a nasal pillows or prongs mask. This means that the velocity of the air may be lower when exiting aperture 128 compared to a nasal prongs or pillows mask. The lower velocity of air exiting the aperture 128 makes it easier for the patient to exhale against the incoming air and also reduces irritation due to high velocity air flow in and around the nose.

3.1.3 Engagement Portions

In the illustrated embodiment, sealing portion 130 may include a nose tip engagement portion 124 and an upper lip engagement portion 126. As shown in FIGS. 3-1 and 3-2, nose tip engagement portion 124 is generally flat or planar along its length so as to provide a sufficiently long sealing surface to accommodate various sized noses. The upper lip engagement portion 126 is more generally curved along its length so as to minimize contact with the patient's upper lip in use.

3.1.4 Nostril Engagement Flaps

In the illustrated embodiments, sealing portion 130 may include nostril engagement flaps 123 structured to align next to or against the nostrils of the patient. In use, flaps 123 seal with the nares (e.g., either directly at the entrance to the nares or along the nostrils of the patient) and flex or bias inwards towards the nose of the patient to stabilize or anchor the seal and enable the sealing portion 130 to fit a variety of nose sizes and shapes. The nostril engagement flaps 123 may be angled in a generally V-shaped orientation.

3.1.5 Flared Sealing Portion

As shown in FIGS. 3-1, 3-2 and 4, the nose tip engagement portion 124, the upper lip engagement portion 126, and the nostril engagement flaps 123 are all structured to curve or extend outwardly from an annular supporting wall or base 133. That is, the nose tip engagement portion 124, the upper lip engagement portion 126, and the nostril engagement flaps 123 are hung or cantilevered from the supporting wall 133 such that they extend or curve outwardly from the supporting wall defining the air path to outer edges of the sealing portion 130 in a continuous, uninterrupted and smooth manner.

3.1.6 Color

The sealing portion 130 may be formed with an opaque material (e.g., silicone) that is not completely clear. Such an opaque material may be achieved by applying a color to the sealing portion 130 to hide the patient's nares from view. For example, when the sealing portion is formed from silicone, the color may be achieved by dispersing a material, e.g., aluminum, in the silicone. The amount and color of the dispersed material can be varied to achieve a desired amount of opaqueness and a desired color.

Various colors may be utilized for the sealing portion 130. For example, the sealing portion may be clear, white, orange, pink, blue, black or any other color. While the sealing portion 130 may be colored, the supporting portion 120 may be a clear or transparent silicone. Alternatively, the supporting portion 120 may also be colored. The supporting portion 120 but may be a contrasting color to the color of the sealing portion 130. When the sealing portion 130 and the supporting portion 120 are formed with different hardness materials, the contrasting colors between the sealing portion 130 and the supporting portion 120 highlight the differences in hardness, although different colors can be used even when the sealing portion 130 and the supporting portion 120 have the same hardness.

3.1.7 Partially Separated Sealing Portion

FIGS. 3-1 and 3-2 show isometric views of sealing portion 130 that is supported or positioned by supporting portion 120. The sealing portion 130 may be separated from the supporting portion 120 by a front gap in an area of a nose tip engagement portion 124 between front anchor points 132, and the sealing portion 130 is connected to the supporting portion 120 on sides of the sealing portion 130 outside the front anchor points 132. Although a sealing portion 130 is shown that is partially separated, a sealing portion without gaps between the sealing portion and the supporting portion may also be used.

The nose tip engagement portion 124 is flexible and can extend downward when contacted by a patient's nose, but will be limited in how far it can extend if it reaches the supporting portion 120. The nose tip engagement portion 124 is extended in length from the aperture 128 to fit nose tips of different size, so that the nose tip of different patients may engage the nose tip engagement portion 124 at different locations. Stem 122 supports the supporting portion 120 and the sealing portion 130. Stem 122 is also adapted to receive the air delivery tube 20 to supply pressurized breathable gas to the patient.

The sealing portion 130, the stem 122, and the supporting portion 120 may be a liquid silicone rubber material or another material, e.g., TPE, gel or foam. The sealing portion 130 may be formed from a material having different properties than the material forming the supporting portion 120 and the stem 122. The stem 122 and the supporting portion 120 may be formed together such as in a mold, and the sealing portion 130 may be formed separately and then joined together with the supporting portion 120, e.g. such as by gluing. Alternatively, the stem 122 and the supporting portion 120 may be formed together such as in a mold, and then the sealing portion 130 may be bonded to the supporting portion 120 and the stem 122 in the mold.

The sealing portion 130 may have different properties than the supporting portion 120 and the stem 122. For example, the sealing portion 130 may be formed from different (or the same) materials, have a different geometry, have a different hardness, than the supporting portion 120 and the stem 122.

The supporting portion 120 and the stem 122 have a hardness that is greater than the hardness of the sealing portion 130 (which as described above may have a hardness of about durometer 5 Shore A), because the supporting portion 120 and the stem 122 both support the sealing portion 130, and provide a reactive force to stabilize the sealing portion 130 in position on the patient's face. For example, the supporting portion 120 and the stem 122 have a hardness of about durometer 20-80 Shore A. Preferably, the supporting portion 120 and the stem 122 have a hardness of about durometer 30-65 Shore A. Most preferably, the supporting portion 120 and the stem 122 have a hardness of about 40 Shore A.

The hardness of the sealing portion 130, the supporting portion 120, and the stem 122 may vary from the hardness levels described, but if so then a thickness of material may need to change to ensure a seal is provided with the patient. For example, the nose tip engagement portion 124 of the sealing portion 130 may have a thickness of 1.2 mm with a hardness of about durometer 5-20 Shore A (preferably about 5-10 Shore A, most preferably about 5 Shore A), but if a harder material is used for the sealing portion 130, then the nose tip engagement portion 124 should have a thickness reduced to, for example, 0.3 mm, so that the same stiffness or reactive force is applied to the patient's face to provide an effective seal.

The supporting portion 120 may include front thickened portion 134 positioned adjacent to an area of the sealing portion that contacts with sides of the patient's nose in use, and transfers headgear load into a pinch force on the sides of a patient's nose to provide an effective seal. The front thickened portion 134 may have a thickness that increases from a top to a bottom, and have a height of about 5 to 20 mm, preferably about 7 to 14 mm, most preferably about 11 mm.

The supporting portion 120 may include rear thickened portion 136. The rear thickened portions 136 may include a lower portion 137 having a first thickness and an upper portion 139 having a second thickness greater than the first thickness. A height of the upper portion 139 may be about 7 to 20 mm, preferably about 8 to 12 mm, most preferably about 9.5 mm, although it could be reduced to about 4 mm to reduce loading. The rear thickened portion 136 may have a curved portion 141, which may have a radius of curvature of about 0.5 to 3 mm, preferably about 2 mm, although it could be increased to about 4 mm to increase stiffness against the upper lip of the patient. The rear thickened portion 136 may include a cored out portion 142 to reduce a bulk of the silicone and to reduce a curing time.

The rear thickened portions 136 are positioned directly below the thickened corner regions 127 of the sealing portion 130, as may be seen in FIG. 3-1. The rear thickened portions 136 transfer a load from the headgear connectors to the thickened corner regions 127 and to the lower corners of the patient's nose to aid in providing an effective seal, and when the headgear is tensioned, the transfer of load to the lower corners of the patient's nose is increased. The bending force from the headgear connectors 138 is transferred in use by the rear thickened portions 136 to the thickened corner regions 127 of the sealing portion 130 to apply a sealing force as an anchor force to regions of the patient's nose adjacent the nasal labial creases. The transfer of force from the headgear connectors 138 to the rear thickened portions 136 may occur due to the stiffened headgear connector arms, which when bent, cause the bending force, and/or by actual contact of the headgear connectors 138 with the rear thickened portions 136.

FIG. 3-2 illustrates another view of the sealing portion 130. The sealing portion 130 is separated from the supporting portion 120 by a rear gap in an area of an upper lip engagement portion 126 between rear anchor points 129, and the sealing portion 130 is connected to the supporting portion 120 on sides of the sealing portion 130 outside the rear anchor points 129. The upper lip engagement portion 126 is flexible and can extend downward when contacted by a patient's upper lip, but will be limited in how far it can extend if it reaches the supporting portion 120.

The nose tip engagement portion 124 is formed as a hanging, flexible membrane. The sides of the sealing portion 130 are connected to or bonded to the supporting portion 130, while there is a front gap between a central portion of the sealing portion 130 and the supporting portion 120 between front anchor points 132. By utilizing this hanging, flexible membrane, the nose tip engagement portion 124 provides a flexible surface that remains in tensile contact with the nose during patient interface movement, and better accommodates varying nose geometries. Different sized noses are provided with a comfortable and effective seal by utilizing a wide nose tip engagement portion 124, which allows the nose tip to be positioned at various locations between the aperture 128 and a front edge of the nose tip engagement portion 124. The nose tip engagement portion 124 may stretch downwards towards the supporting portion 120 depending on the size of the patient's nose.

The sealing portion 130 includes two thickened corner regions 127 positioned on each side of the upper lip engagement portion 126. The thickened corner regions 127 are adapted to seal with the patients face in use at regions of the patient's nose adjacent the nasal labial creases. The two thickened corner regions 127 protrude outward to provide an effective seal in this area. The two thickened corner regions 127 may each have a radius of curvature of between about 2.4 mm and about 6 mm. A radius of curvature of the upper lip engagement portion 126 may be about 5 mm.

A thickness of the thickened corner regions 127 of the sealing portion 130 could be about 1 to 5 mm, preferably about 2 to 4 mm, most preferably about 3.5 mm with a relatively low durometer Shore A hardness for comfort. The thickness could be increased up to about 5 to 10 mm, preferably about 5 to 8 mm, most preferably about 5 mm depending on the thickness of the underlying supporting portion 453, and could be decreased to a same thickness as the upper lip engagement portion 126, about 0.25 to 3 mm, preferably less than 2 mm, most preferably about 1.2 mm.

The distance between the unbonded region of the sealing portion 130 at the upper lip engagement portion 126 and the supporting portion 120 may be about 1 to 15 mm, preferably about 5 to 10 mm, most preferably about 7 mm when not in use, and may vary between 0 mm and 15 mm, preferably up to 7 mm in use based on contact seal force to the philtrum of the patient. The distance between the top edge of the sealing portion 130 and the supporting portion 120 may be about 10 to 30 mm, preferably about 15 to 20 mm, most preferably about 18 mm. The width of the upper lip engagement portion 126 may be about 10 to 30 mm, preferably about 15 to 25 mm, most preferably about 20 mm, but this could be varied between about 14 mm and about 22 mm depending on nose width. A radius of curvature at the center of the upper lip engagement portion 126 may be about 5 to 20 mm, preferably about 10 to 15 mm, most preferably about 12.5 mm when not in use, but will lessen when in use and with inwards flex of the mask 110.

The sealing portion 130 is thus connected to the supporting portion 120 on both sides, but is separated by gaps from the supporting portion 120 between the front and rear anchor points 132, 129. These gaps allow the sealing portion 130 to flex in use at the nose tip and upper lip regions of the patient to provide a good fit and comfort to the patient.

Figure 4:
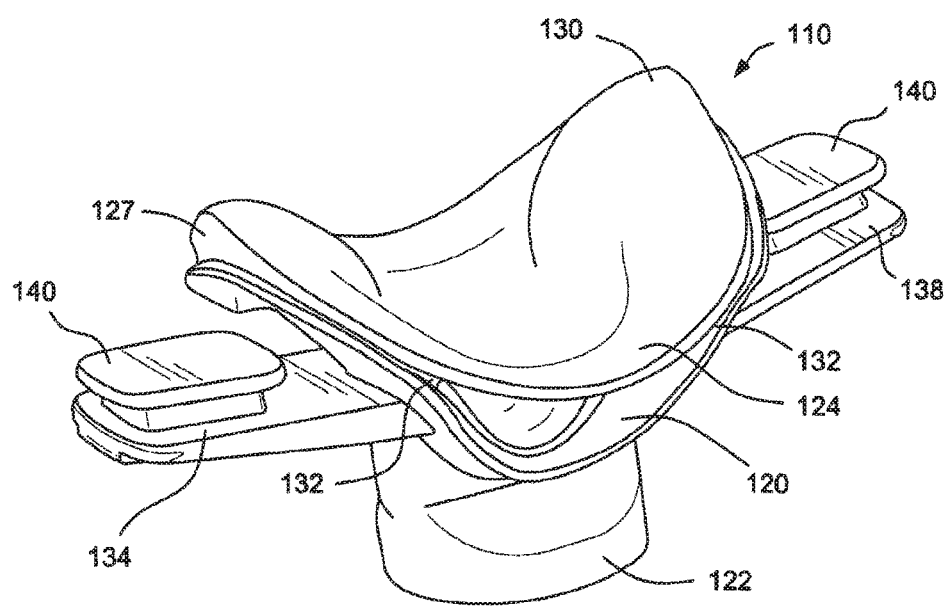
FIG. 4 is an isometric views of a sealing portion of a patient interface according to an embodiment of the present technology.

As shown in FIG. 4, mask 110 may include headgear connectors 138. The headgear connectors 138 may include tabs 140. The tabs 140 may provide connection points for connecting headgear. The headgear connectors 138 may be molded together with the stem 122. Alternatively, headgear connectors 138 may be removably attachable to stem 122 and/or the supporting portion 120. For example, headgear connectors 138 may be clipped, wrapped or otherwise connected to the stem 122.

Headgear connectors 138 may have a hardness of about durometer 20 to 80 Shore A, preferably about 20 to 60 Shore A, and most preferably about 40 Shore A. The geometry of the supporting portion 120 may be adjusted to be molded with the headgear connectors 138.

3.2 Facial Pad

Figures 1, 5:
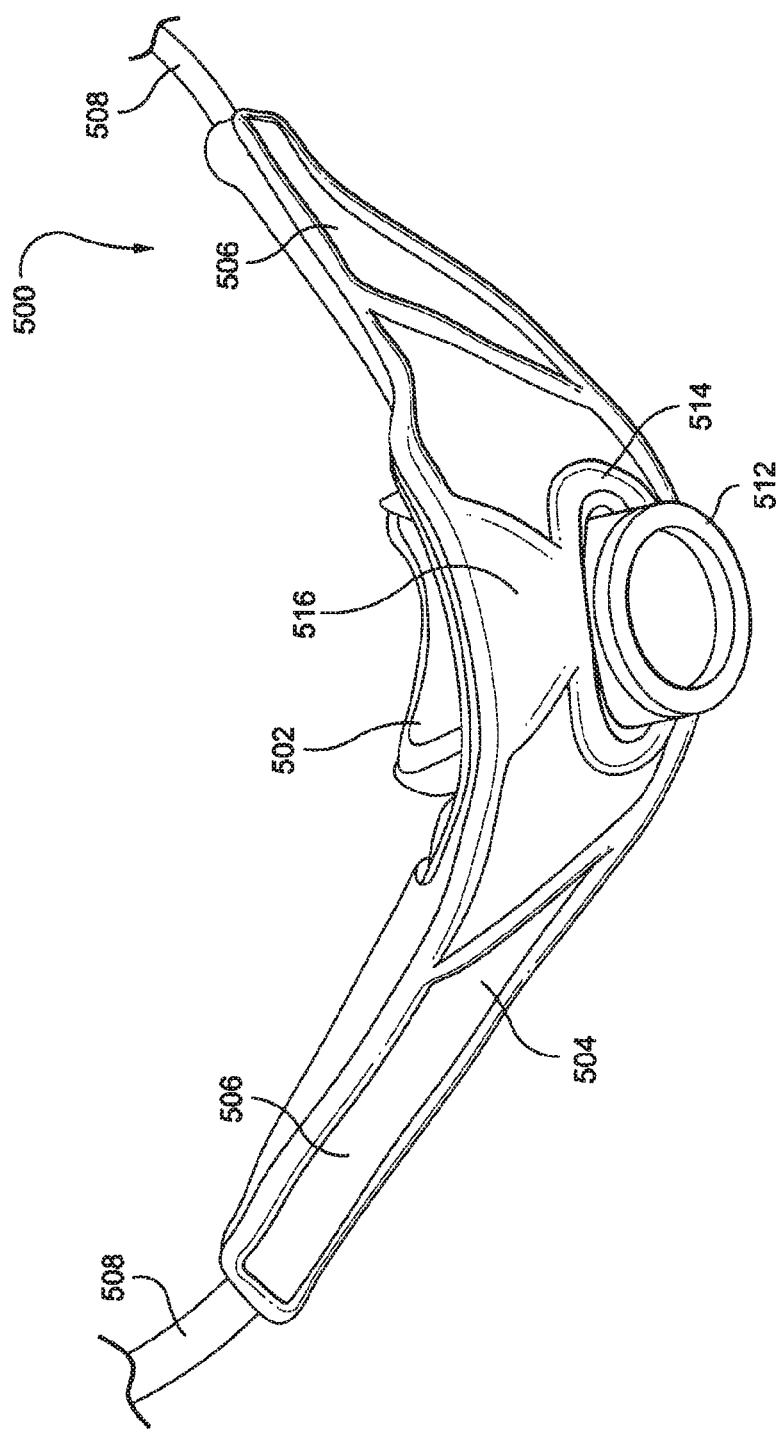
FIG. 5 is a front view of a patient interface on a model patient according to another embodiment of the technology in use on a patient.
Figures 2, 5:
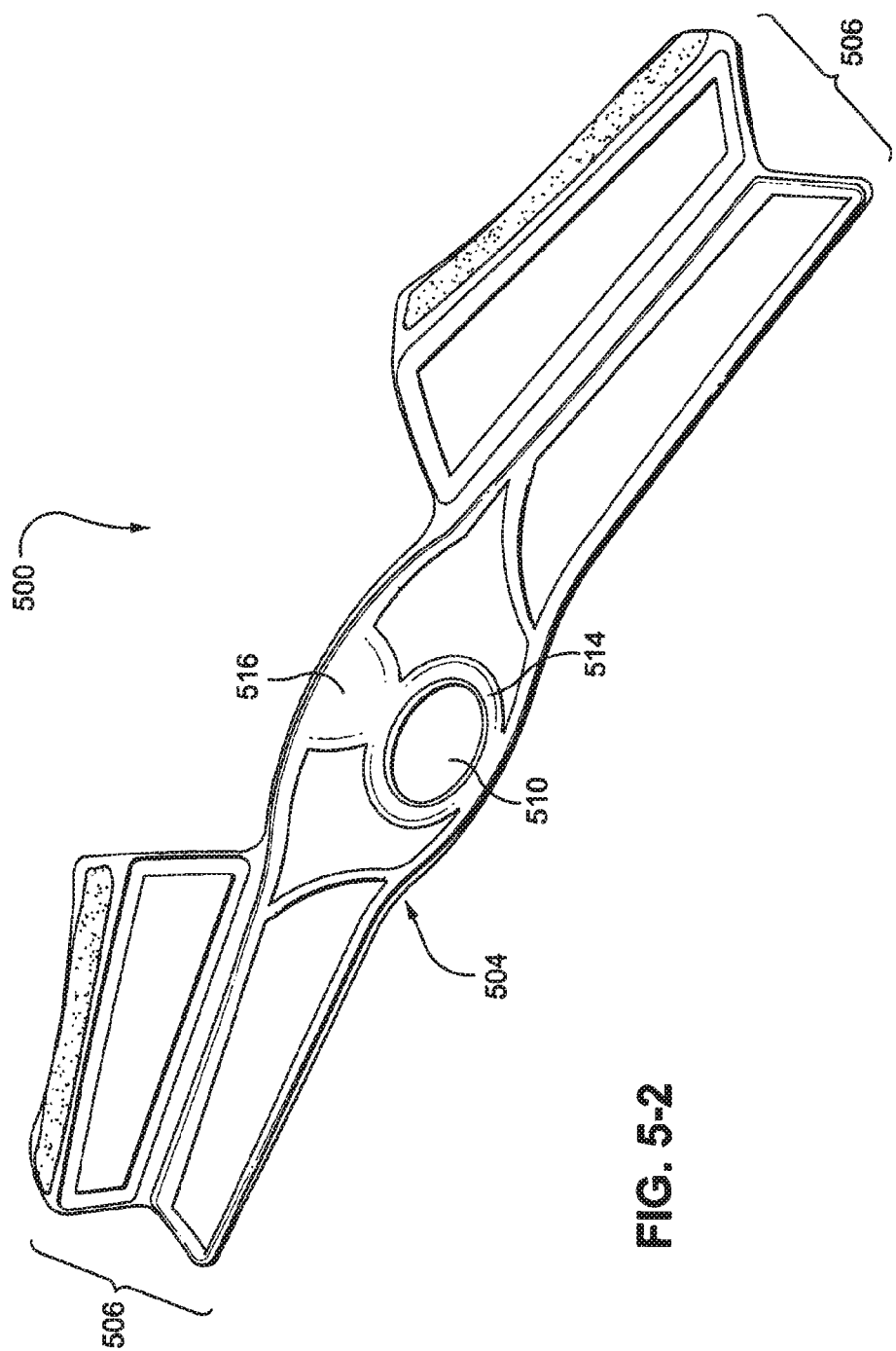

As illustrated in FIG. 5, a patient interface 200 includes a mask 202, headgear 203 and facial pad or cover 206. The headgear may be adjustable at least at a top of the patient's head with an adjustable connector 214. The patient interface 200 is connected to elbow 204 and air delivery tube 220 to deliver air to the patient interface 200.

The facial pad 206 may be utilized to improve patient comfort and reduce facial marking. The facial pad 206 may be formed of a material that is comfortable to the patient, e.g., cloth, although other materials may be used to vary breathability, obtrusiveness, and/or indicate alignment.

The facial pad 206 may be formed in one piece and shaped to fit over (slip over) the mask 202 and a portion of the headgear 203 that comes into contact with the patient's face. The facial pad 206 may completely surround the mask 202, and be positioned between the patient and the mask 202 in use to provide a more comfortable interface to the patient. However, it should be appreciated that the facial pad 206 may be structured to cover one or more portions of the mask 202 and/or headgear 203. The facial pad 206 may also completely surround at least a portion of the headgear 203. The facial pad 206 may include an opening in a back portion for insertion of the mask 202. The facial pad 206 may include openings at each end into which the end portions of the headgear to be attached to the mask 202 are inserted.

The facial pad 206 may include a shroud portion 208, which may cover over the nose portion of the mask 202, to hide the nose area of the patient that forms a seal with the mask 202. The facial pad 206 may include edges stitched together or ultra sonically welded or otherwise joined to form the desired shape to fit the mask 202 and headgear 203. Hook and loop material may be used on the facial pad 206 and the shroud portion 208 to secure them together around the mask 202.

The facial pad 206 may alternatively be formed in more than one piece. For example, the shroud portion 208 may be a separate piece from the rest of the facial pad 206. In this case, the shroud portion 208 may attach to the remaining portion of the facial pad 206 by conventional means, e.g., hook and loop material on the facial pad 206 and the shroud portion 208.

Thermoformed Headgear Wrap

FIGS. 5-1 and 5-2 show an example headgear wrap 500. FIG. 5-1 shows the headgear wrap 500 with a cushion 502, while FIG. 5-2 shows the headgear wrap 500 in isolation. Headgear wrap may be thermoformed to increase stiffness in particular regions, aid in providing a pre-determined shape to the wrap (to assist in ensuring the mask is sealing) and also for aesthetics.

Headgear wrap 500 includes a flexible region 504 (which may be of relatively less thickness) to permit wrap to flex to hug the patient's face in use. Wrap 500 includes a wrapping portion 506 on each side that includes one or more folds where the wrap fits around headgear straps 508. A central portion of the wrap includes an aperture 510 to receive a connecting portion 512 of the mask cushion 502, with the aperture including a bead 514 around at least a portion of its perimeter for added stiffness. Headgear straps 500 extend from each side of the wrap. Wrap 500 may include a support cushion 516 (of relatively greater thickness) to seal with the patient's nose tip, which support cushion may be contiguous with the bead 514.

FIG. 5-2 shows the wrap in isolation, where wrapping portions are in an open position in which case the headgear straps can be placed in position, and then the wrapping portions can be folded over and the hook material portion connected to the loop material portion of the wrap to secure the headgear and the mask in position.

3.3 Alignment and/or Orientation Indicators

The masks illustrated herein include detachable headgear including straps that attach to respective sides of the mask. If the patient is not familiar with the mask, the patient may try to connect the headgear to the incorrect sides of the mask. Additionally, the patient may try to put the mask on upside down. Accordingly, the mask may include alignment and/or orientation indicators to assist the patient in correct assembly of the headgear to the mask and to assist the patient with putting on the mask right side up.

For example, the facial pad 206 may include alignment and/or orientation indicators. For example, as illustrated in FIG. 5, an alignment and/or orientation indicator could be the location of stitching 210, with the stitching 210 placed at a front portion of the facial pad 206. A brand indicator 212 may be disposed on the facial pad 206, to indicate a brand or name of the facial pad 206 or of the mask 202. The brand indicator 212 could also act as an alignment and/or orientation indicator, so that each side of the facial pad 206 is correctly aligned with the correct side of the headgear 203 such that the brand indicator 212 is placed on a front side of the mask 202 and not upside down when the correct sides of the headgear 203 are place inside the correct sides of the facial pad 206. The brand indicator 212 may be an orientation indicator, e.g., a left side or right side indicator. The facial pad 206 could also include printing or marking to indicate correct alignment with the headgear 203 and mask 202, e.g., a left side or right side indicator.

FIGS. 6-1 to 6-8 illustrate patient interfaces 240 that include masks 242 and headgear 245. Each mask 242 includes may include the features of the mask 110 of FIGS. 1-4, and includes a sealing portion 244. The masks 242 may include alignment and/or orientation indicators. The size indicators 246 and brand indicators 248 can be used to indicate a size and a brand, respectively, but can also act as orientation indicators, in that the user can put on the mask with the text of the size indicator 246 and/or the brand indicator 248 right side up and have the mask correctly oriented.

As illustrated in FIGS. 6-2, 6-3, 6-4, 6-6, 6-7 and 6-8, orientation indicators 254 may be directional indicators, e.g., upwardly pointing shapes, indicating a top side of the mask that may be perceived by the patient so that the mask 242 may be put on with a correct orientation. The shapes of the depicted orientation indicators 254 include triangles, and one or more v-shaped elements, although any directional indicator could be used, such as other shapes or words. Either of the brand indicator 248 or the orientation indicator 354 could be omitted, with the remaining one of the brand indicator 248 and the orientation indicator 354 used for orientation of the mask 242.

Figures 1, 6:
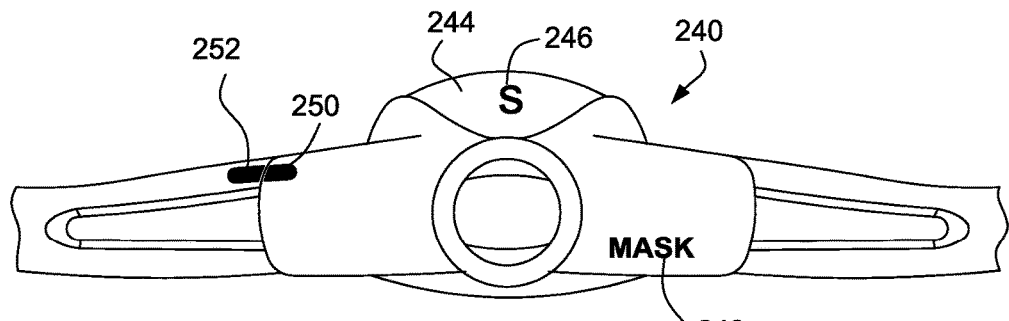
Figures 2, 6:
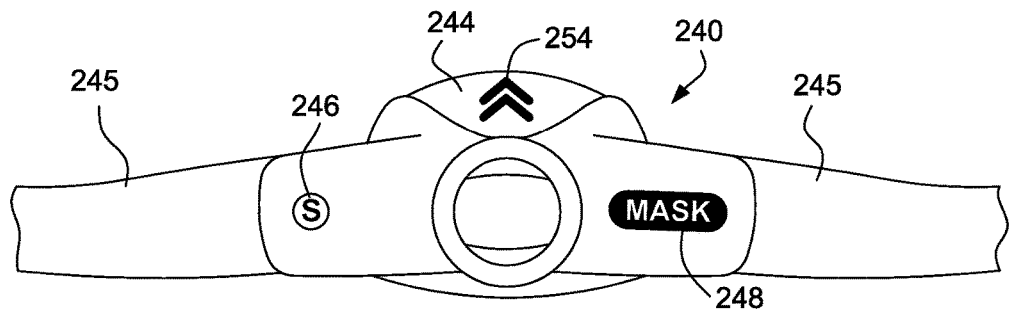
Figures 3, 6:
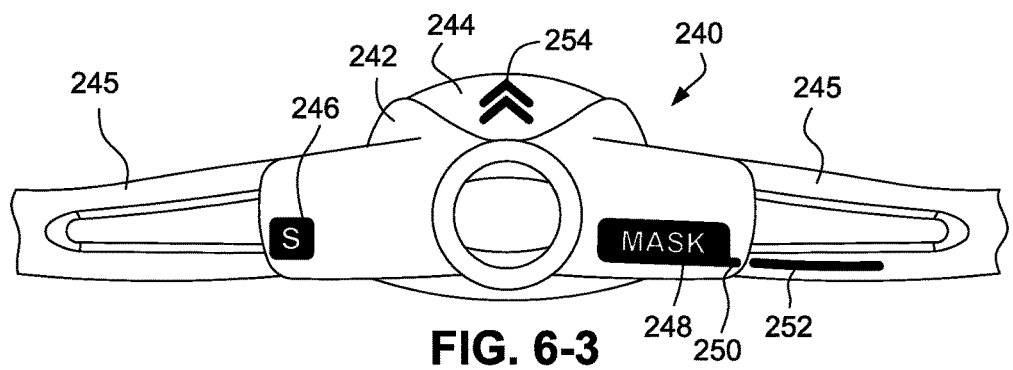
Figures 4, 6:
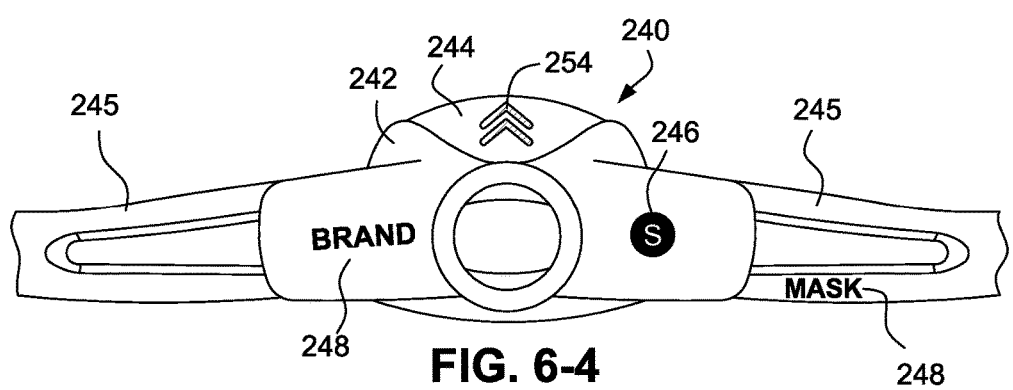
Figures 5, 6:
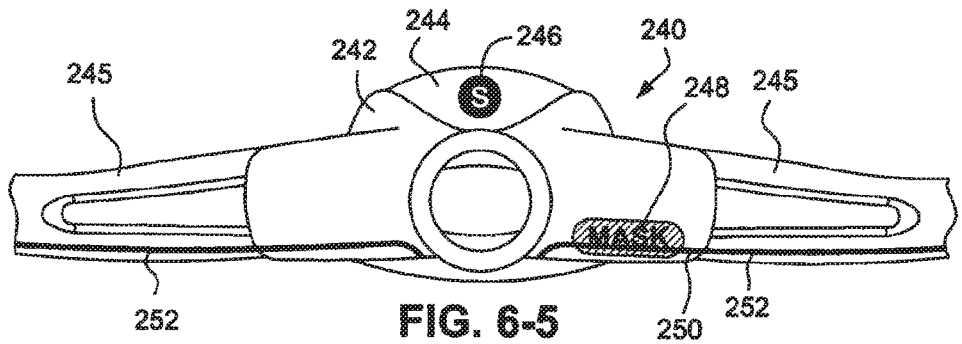
Figure 6:
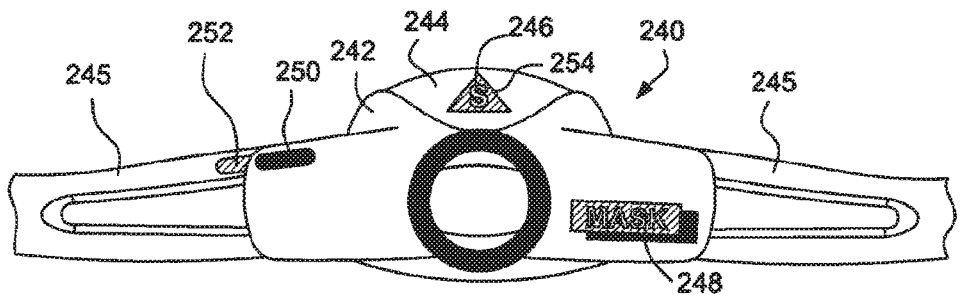

The patient interface 240 may include alignment indicators 250 and 252, with the alignment indicator 250 included on the mask 242, and the alignment indicator 252 on the headgear 245. When the headgear 245 is attached to the mask 242, the patient aligns the alignment indicator 250 with the alignment indicator 252, which allows the patient to connect the headgear 245 to the correct sides of the mask 242. The alignment indicators 250 and 252 may be on both sides of the patient interface 240 as illustrated in FIG. 6-5, or only on one side of the patient interface 240, as shown in FIGS. 6-1, 6-3 and 6-6.

The alignment indicators 250 and/or 252 can also act as orientation indicators. For example, in FIGS. 6-1 and 6-6, the alignment indicator 250 and the alignment indicator 252 are disposed on an upper side of the patient interface 240, which can function as orientation indicators indicating the patient interface 240 should be put on the patient with the alignment indicator 250 and the alignment indicator 252 in the upper part of the patient interface 240 as illustrated in FIGS. 6-1 and 6-6. The alignment indicators 250 and 252 can also be placed on a lower side of the patient interface 240, as illustrated in FIGS. 6-3 and 6-5 to show a bottom orientation.

The size indicators 246, brand indicators 248, alignment indicators 250, 252, and orientation indicators 254 may be disposed on the patient interface 240 in colors contrasting with the patient interface 240 to be readily visible. In addition, as illustrated in FIGS. 6-6 and 6-7, the brand indicators 248 may include a shadow type image for distinctiveness.

Figures 6, 7:
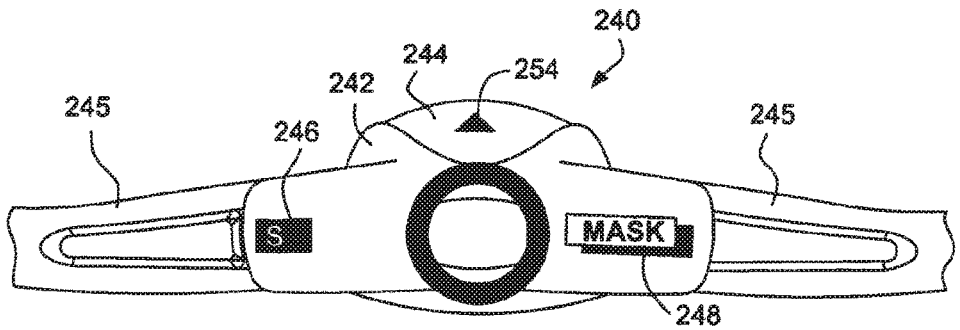

FIG. 7 illustrates a patient interface 300 on a model patient. The patient interface has a mask 310 and headgear 314 for securing the mask 310 to the patient's head. The mask 310 may include the features of the mask 110 of FIGS. 1-4, and includes a sealing portion 312 and headgear connectors 316 for connecting the headgear 314 to the mask 310. Elbow 322 may be disposed between the mask 310 and the air delivery tube 320. The headgear may include a front portion 315 that extends in use from the headgear connectors 316 between the patient's eyes and ears on each side of the patients head and connects at the top portion of the patient's head. An adjustable connector 321 may allow the adjustment of the headgear to fit the patient. The headgear 314 may include a back of head portion 324 that connects to the front portion 315, such as through a slot formed in the front portion 315, and wraps around the back of the patient's head.

Figures 6, 7, 8:
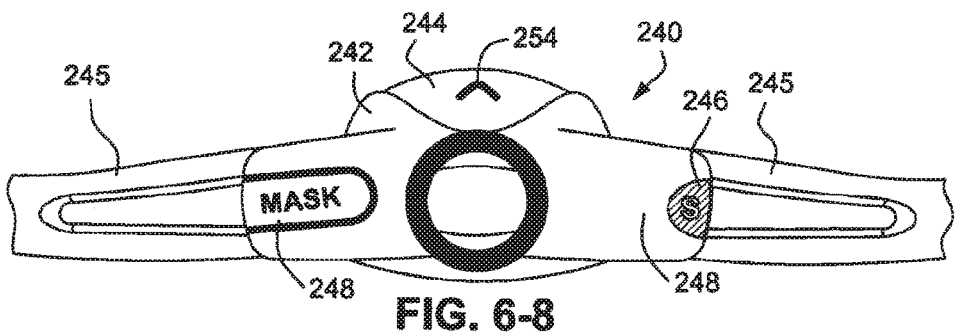
Figure 7:
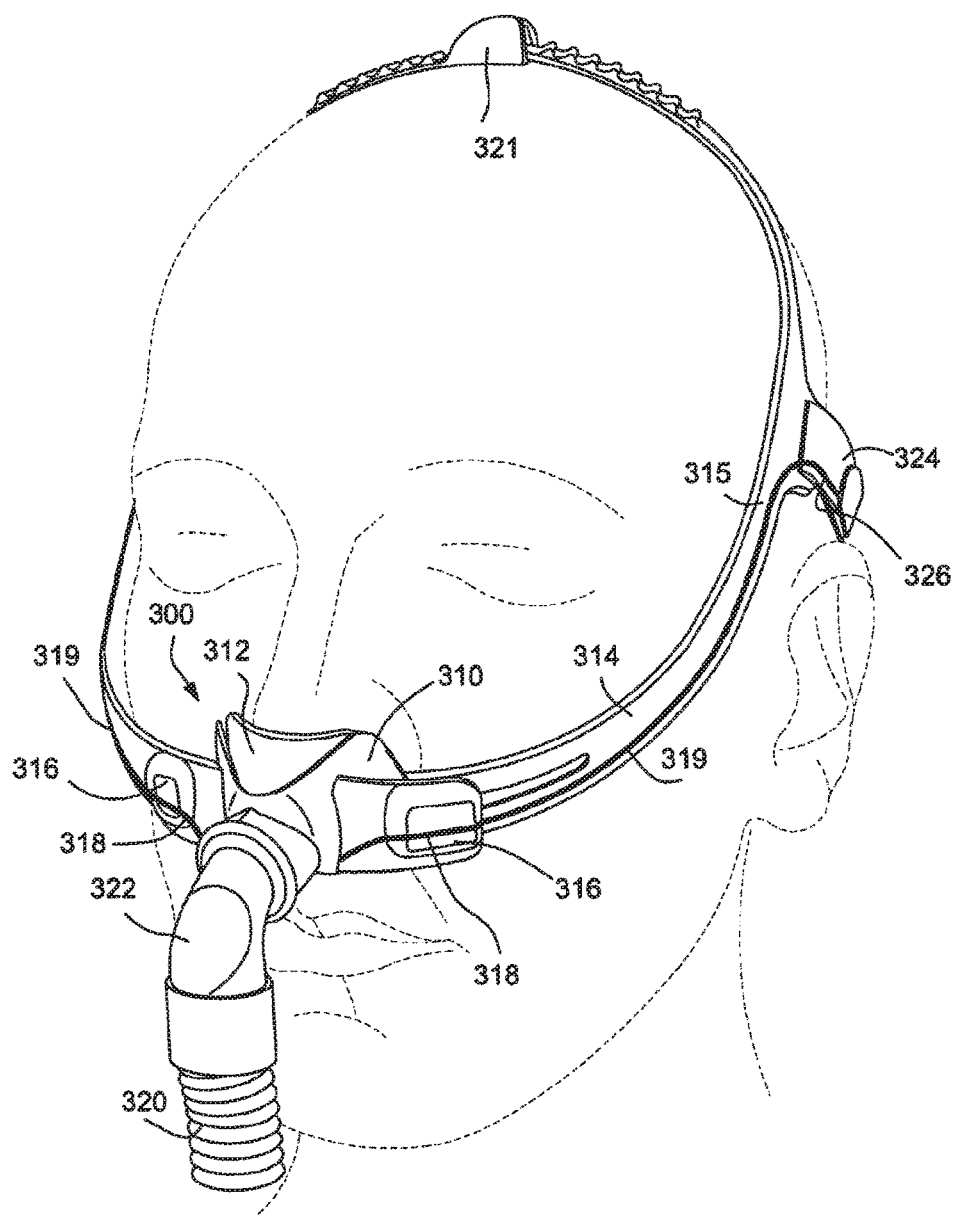
Figure 8:
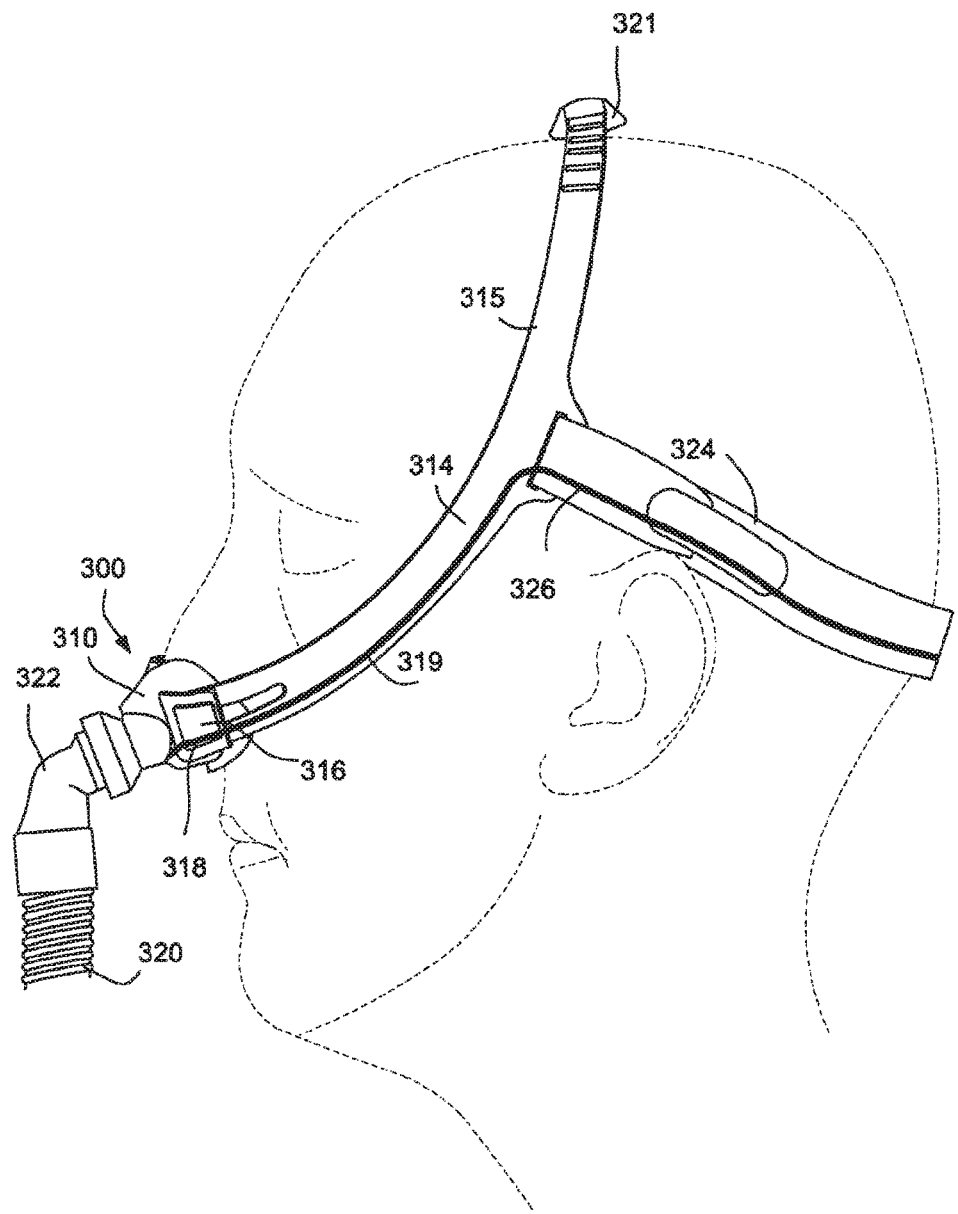

The patient interface 300 may include orientation and/or alignment indicators such as any of those illustrated in FIGS. 6-1 through 6-8. For example, as shown in FIGS. 7 and 8, alignment indicators 318, 319 and 326 may be formed on the mask 310, the front portion 315 of the headgear 314, and the back of head portion 324 of the headgear 314, respectively. When the back of head portion 324 of the headgear is connected to the front portion 315, the patient aligns the alignment indicator 326 with the alignment indicator 319, which allows the patient to connect the back of head portion 324 to the correct sides of the front portion 315 of the headgear. When the headgear 314 is connected to the headgear connectors 316, the patient aligns the alignment indicator 319 with the alignment indicator 318, which allows the patient to connect the headgear 314 to the correct sides of the mask 310.

The alignment indicators 318, 319 and 326 may be disposed on only one side of the patient interface 300, or as shown in FIG. 7 may be on both sides of the patient interface 300. When the alignment indicators 318, 319 and 326 are on both sides of the patient interface 300, after the headgear 314 is properly connected to the mask 310, the alignment indicators 318, 319 and 326 form a continuous line over 3 components of the patient interface, the mask 310, the front portion 315 of the headgear and the back of head portion 324 of the headgear. The continuous line traverses the mask 310 on a first side of the patient interface 300, along the front portion 315 of the headgear on the first side of the patient interface 300 to the back of head portion 324 of the headgear, around the patient's head on the back of head portion 324 of the headgear, to the front portion 315 of the headgear on a second side of the patient interface 300, and to the mask 310 on the second side of the patient interface 300.

The alignment indicators 318, 319 and 326 may also function as orientation indicators. For example, as shown in FIGS. 7 and 8, the alignment indicators 318, 319 and 326 may be disposed on a lower portion, e.g., lower half, of the mask 310, the front portion 315 of the headgear 314, and the back of head portion 324 of the headgear 314, respectively, to indicate a lower side of those components. The alignment indicators 318, 319 and 326 could also be place on an upper portion of the respective components to indicate an upper side of the respective components.

The alignment, orientation, size and brand indicators may be molded and/or printed onto and/or into the mask. Further, the alignment orientation, size and brand indicators may be molded, printed, stitched, embossed or otherwise formed on the headgear.

Figure 9:
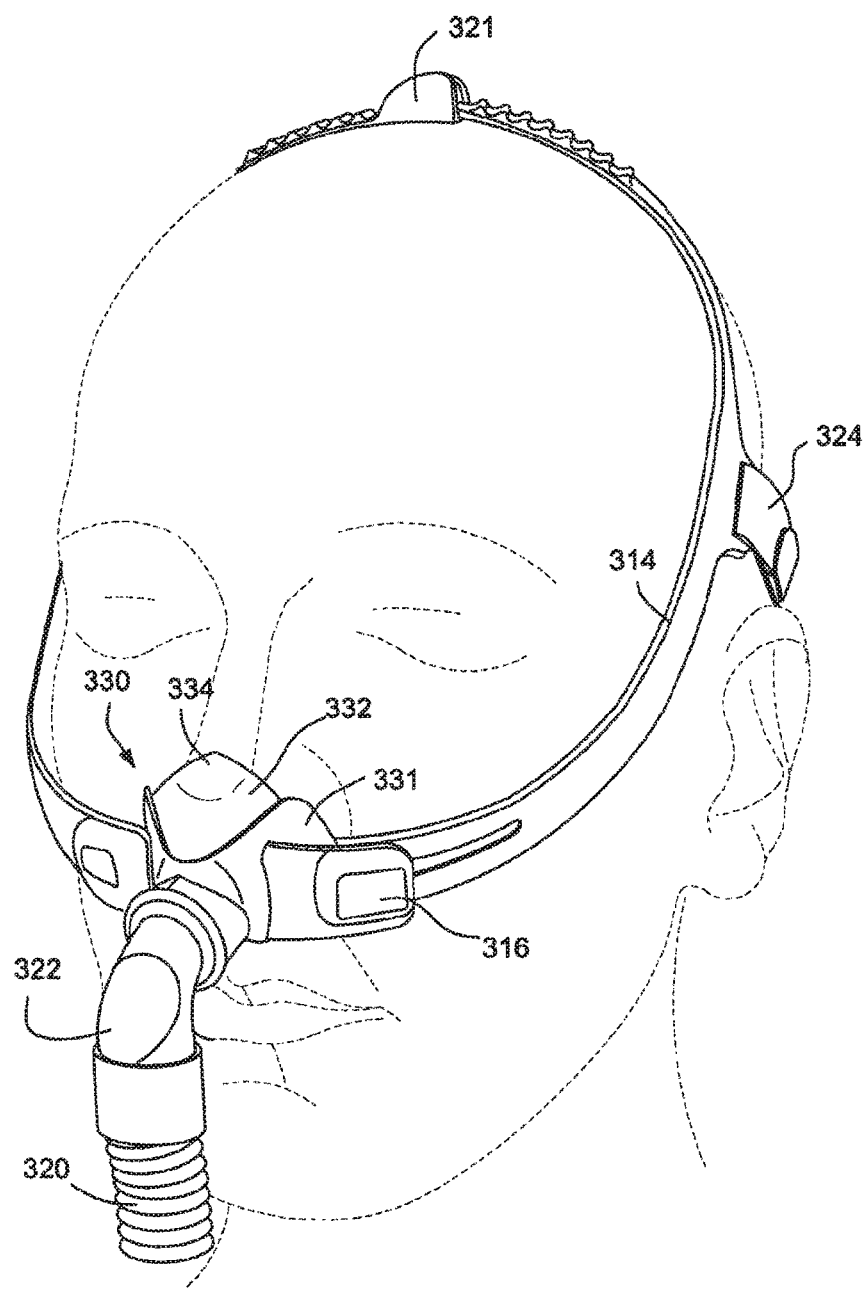
FIG. 9 is a front perspective view of a patient interface with an orientation indicator on a model patient according to an embodiment of the present technology.

FIG. 9 illustrates a patient interface 330 that includes mask 331 and headgear 314 adapted to secure the mask 331 to the patient's head in use. The mask 331 includes a sealing portion 332. The sealing portion 332 is adapted to include a shape that functions as an orientation indicator. In particular, the sealing portion 332 (or a supporting portion) may be formed with a shape including a directional orientation, e.g., a peak, triangle, or an inverted v shape, to indicate a top side of the patient interface 330 or mask 331. The peak, triangle, or inverted v shape is selected to provide an intuitive directional orientation for the patient so that the patient will orient the mask correctly.

Figure 10:
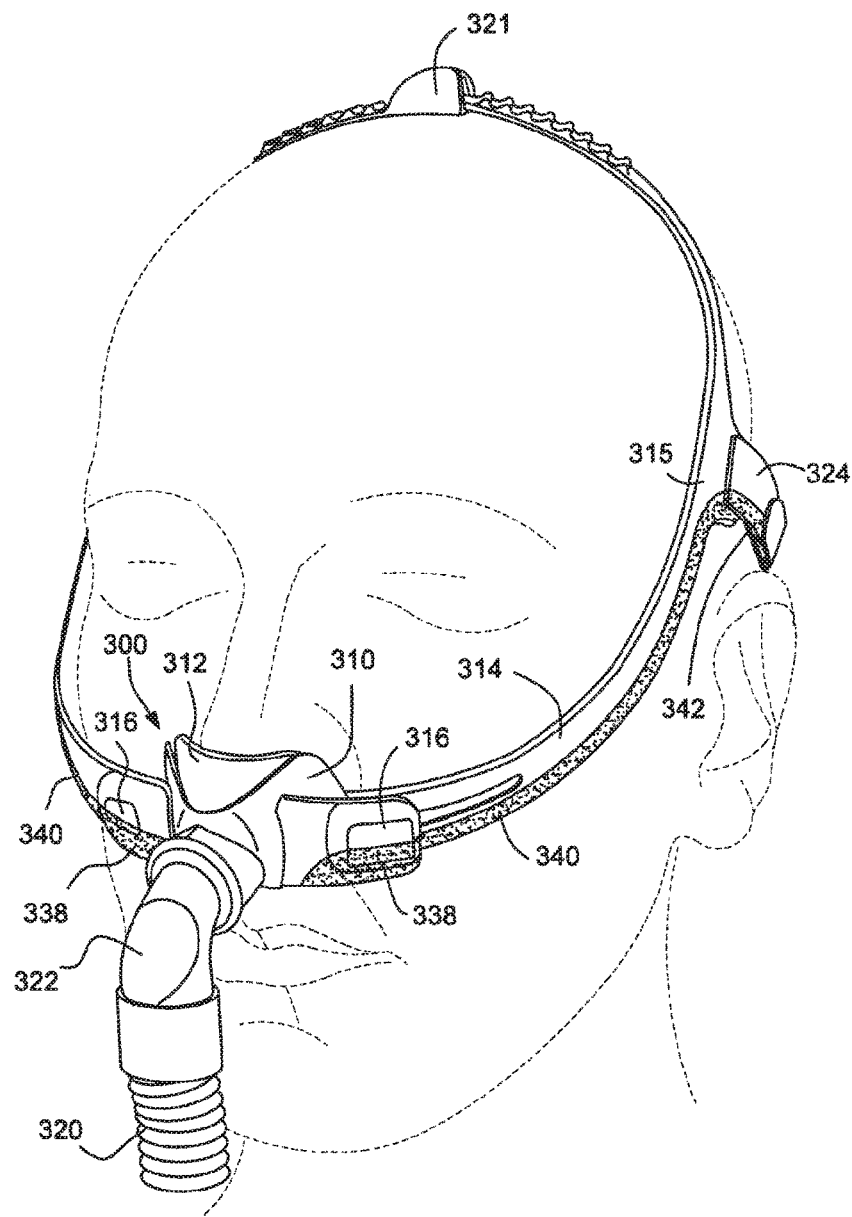
FIG. 10 is a front perspective view of a patient interface with an alignment indicator on a model patient according to an embodiment of the present technology.
Figure 11:
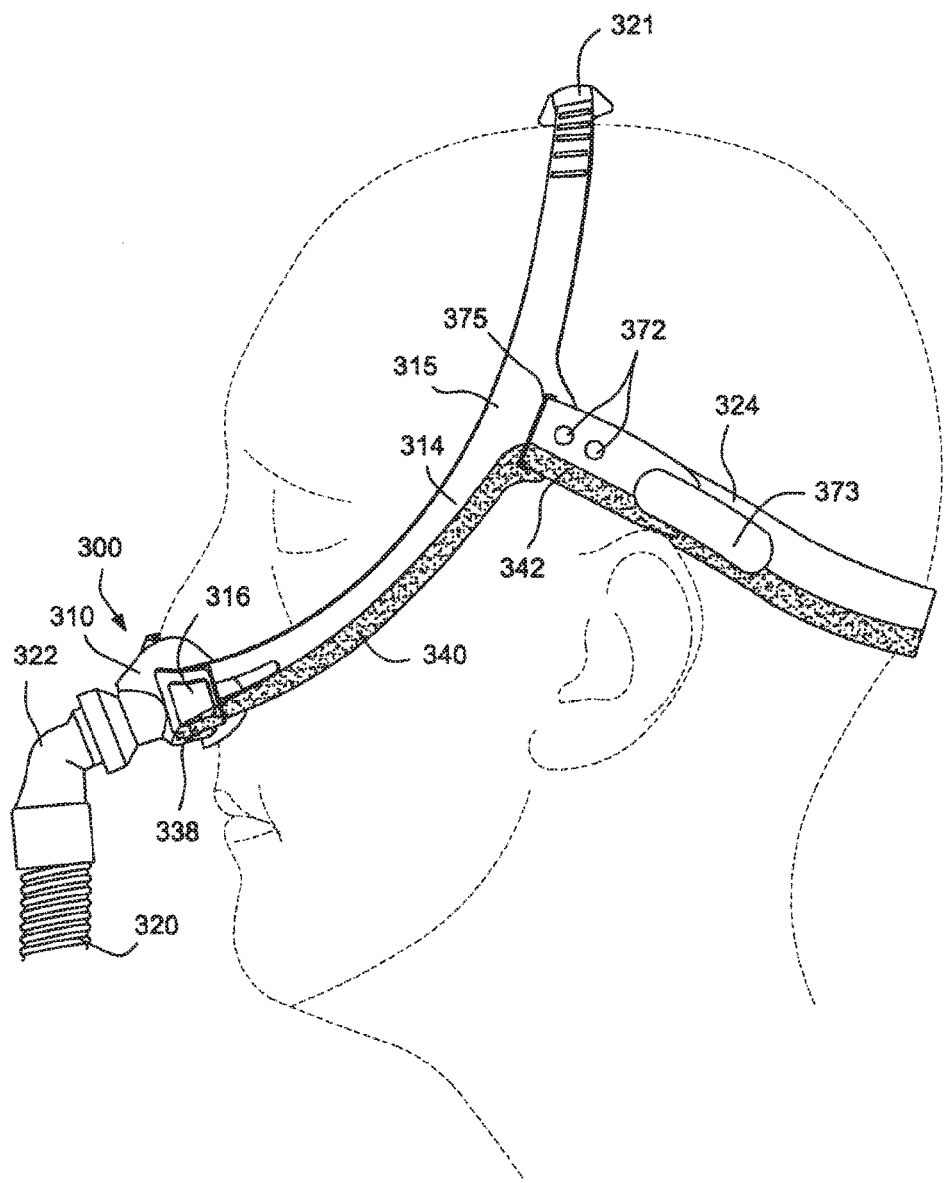
FIG. 11 is a side view of the patient interface of FIG. 10 on a model patient.

FIGS. 10 and 11 illustrate a patient interface 300 including another form of alignment indicator. Alignment indicators 338, 340 and 342 may be formed on the mask 310, the front portion 315 of the headgear 314, and the back of head portion 324 of the headgear 314, respectively. The alignment indicators 338, 340 and 342 may be disposed on only one side of the patient interface 300, or as shown in FIG. 10 may be on both sides of the patient interface 300.

The alignment indicators 338, 340 and 342 may be formed with a common texture or common color. For example, a subtle frosted finish may be used for the alignment indicators 338, 340 and 342. The common texture or color may contrast with the color and/or texture of the mask 310, the front portion 315 of the headgear 314, and/or the back of head portion 324 of the headgear 314. The common texture or color may be molded, printed, stuck or otherwise attached to the mask 310, the front portion 315 of the headgear 314, and the back of head portion 324 of the headgear 314. The common texture or color may also be the addition of material to the components, with the added material possessing the common texture or common color.

When the back of head portion 324 of the headgear is connected to the front portion 315 of the headgear, the patient aligns the alignment indicator 342 with the alignment indicator 340, which allows the patient to connect the back of head portion 324 to the correct sides of the front portion 315 of the headgear. When the headgear 314 is connected to the headgear connectors 316, the patient aligns the alignment indicator 340 with the alignment indicator 338, which allows the patient to connect the headgear 314 to the correct sides of the mask 310.

The alignment indicators 338, 340 and 342 may also function as orientation indicators. For example, as shown in FIGS. 10 and 11, the alignment indicators 338, 340 and 342 may be disposed on a lower portion, e.g., lower half or lower third, of the mask 310, the front portion 315 of the headgear 314, and the back of head portion 324 of the headgear 314, respectively, to indicate a lower side of those components. The alignment indicators 338, 340 and 342 could also be place on an upper portion of the respective components to indicate an upper side of the respective components.

Figures 1, 12:
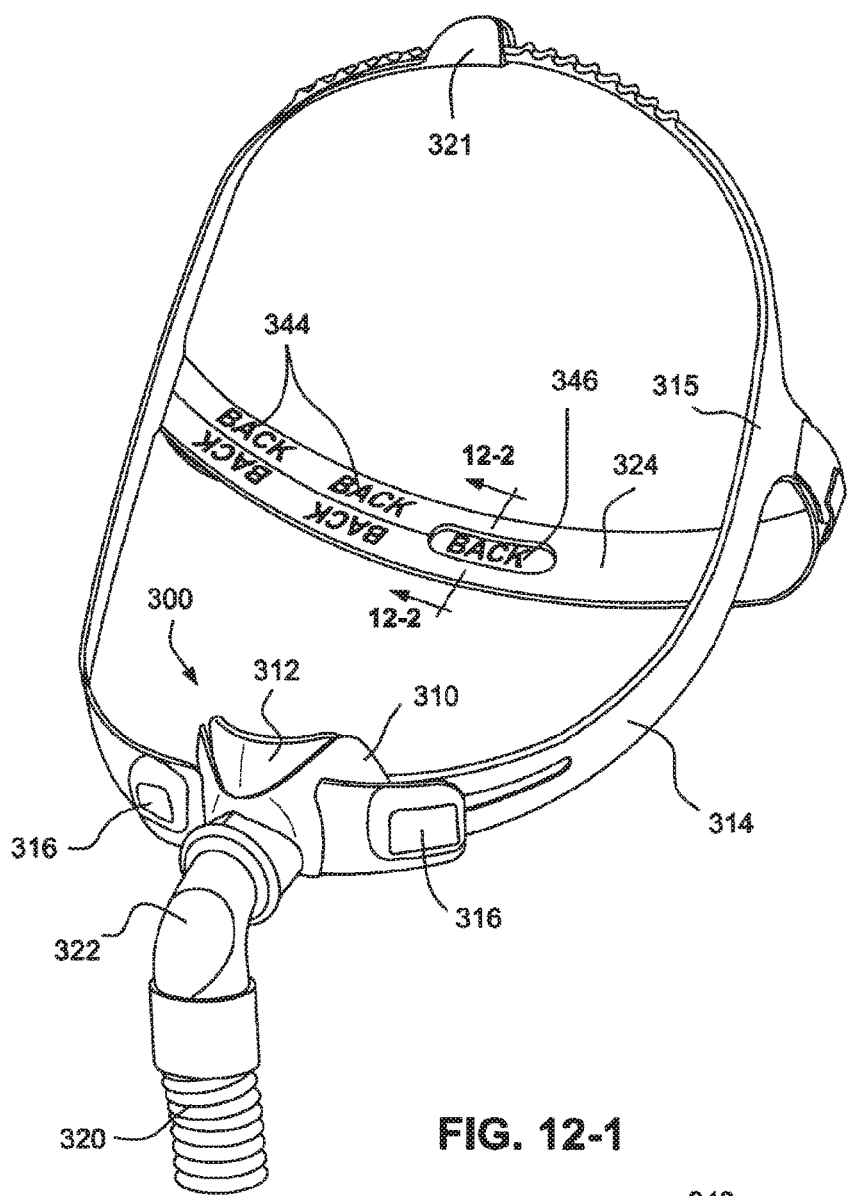
Figures 2, 12:
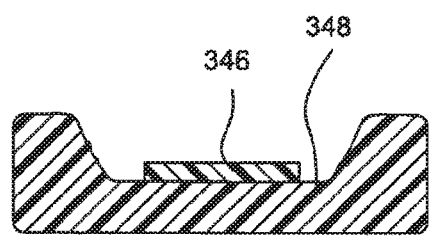

FIG. 12-1 illustrates a patient interface 300 with orientation indicators 344, 346. The orientation indicators 344 include printing or other marking to indicate orientation. For example, the orientation indicators may include printing such as "back" to indicate the strap is the back strap. Additionally, the orientation indicators may be placed on a particular side of a strap for orientation purposes, such as placing the printing on the side of a strap that will contact the patient, or on an opposite side. The orientation indicators may include a double printing, with the same printing printed in a first orientation and then printed in an upside down fashion from the first orientation. This double printing can intuitively indicate to the patient that the strap may be used with either of the two printings right side up. Any of the orientation indicators may be combined with other features described herein, such as the alignment indicators.

The orientation indicator 346 may be an embossed orientation indicator, as illustrated in FIGS. 12-1 and 12-2. The embossing of the orientation indicator may provide the advantage of not irritating the patient, as the embossed printing is formed in a depression 348 formed in strap 324, and thus avoids contact of the orientation indicator 346 with the patient.

Figures 1, 13:
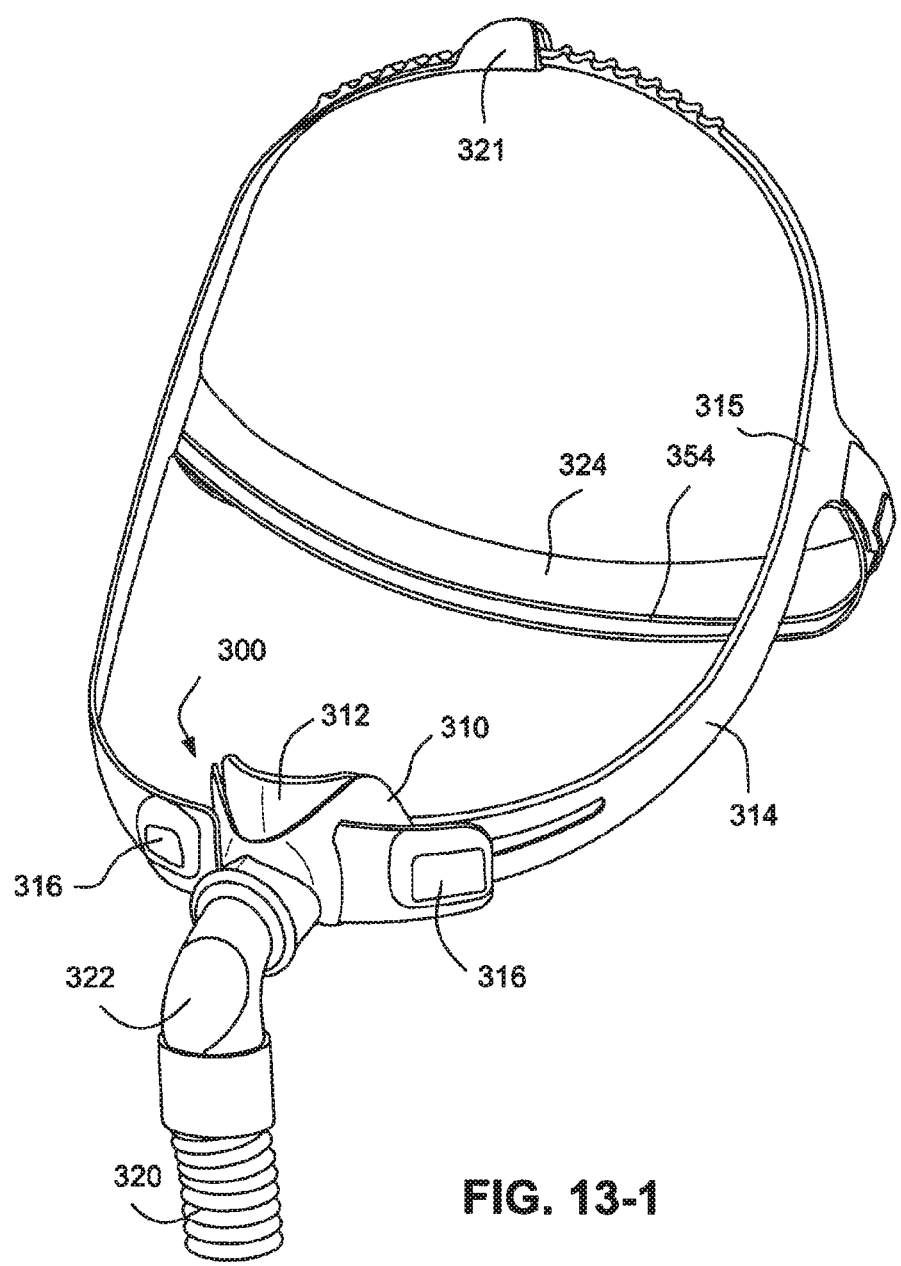
Figures 2, 13:
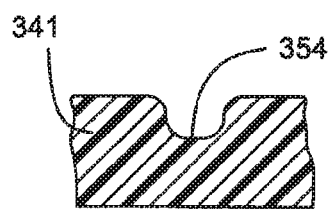
Figures 3, 13:
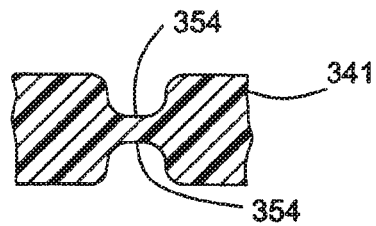

FIG. 13-1 illustrates a patient interface 300 with an orientation indicator 354. The orientation indicator may be in the form of a line. The orientation indicator 354 may be placed on a particular side of a strap for orientation purposes, such as placing the line on the side of a strap that will contact the patient, or on an opposite side. The orientation indicator 354 may be an embossed orientation indicator, as illustrated in FIGS. 12-1 and 12-2, and may be on one or both sides of the back of head portion 324 of headgear 314. The orientation indicator 354 may also be in the form of a raised line, and may provide a gripping portion.

Figures 1, 14:
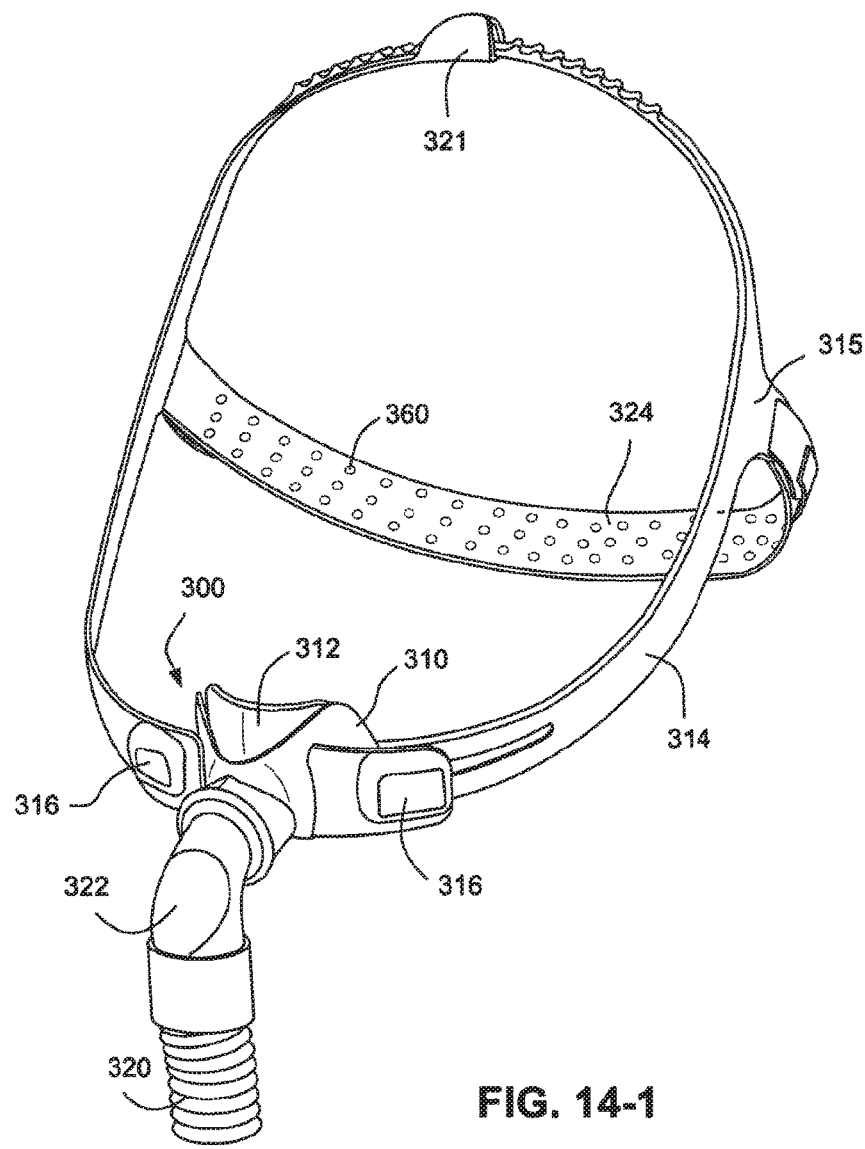
Figures 2, 14:
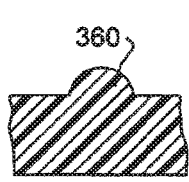
Figures 3, 14:
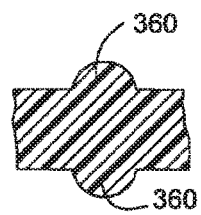
Figures 4, 14:
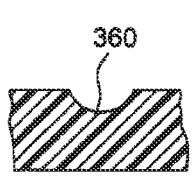
Figures 5, 14:
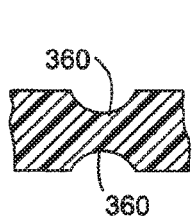
Figures 6, 14:
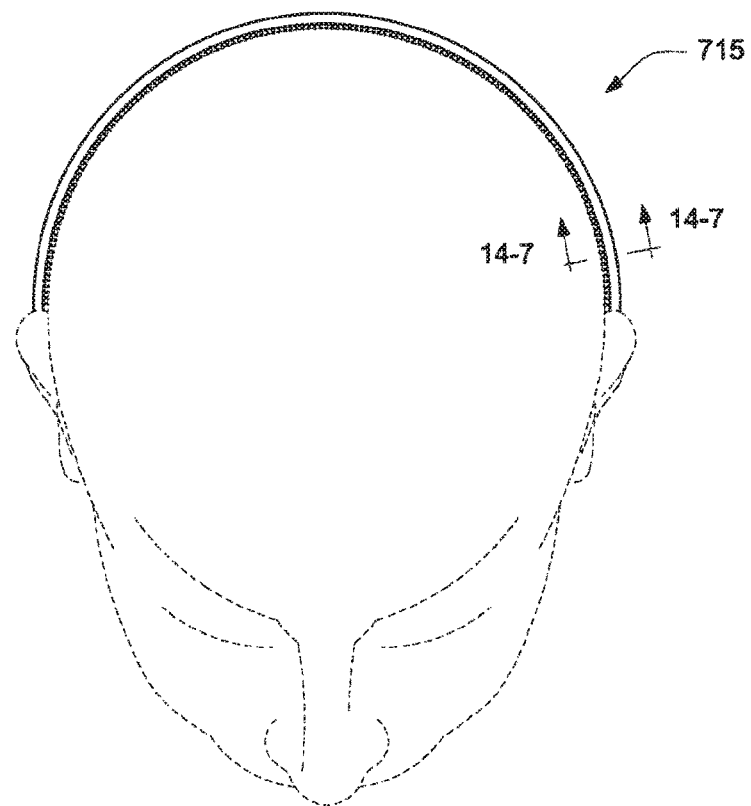
Figures 7, 14:
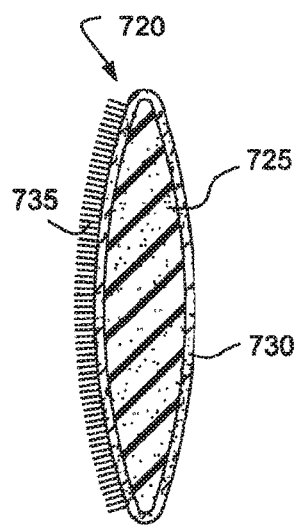
Figures 8, 14:
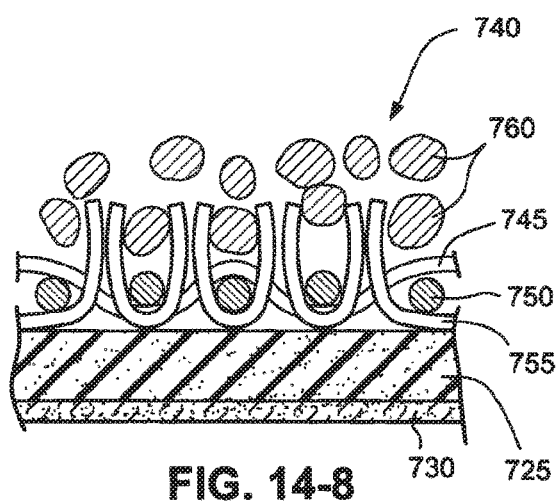

FIG. 14-1 illustrates a patient interface 300 with tactile orientation indicators 360. The tactile orientation indicators 360 are tactile elements, (e.g., raised or indented portions) that provide a tactile feedback to the patient. The tactile orientation indicators 360 may be provided on the headgear 314 or on the mask 310. For example, as shown in FIG. 14-1, the tactile orientation indicators 360 are provided on a side of the back of head portion 324 of headgear 314, and may be used to indicate orientation of the back of head portion 324 of headgear 314, such as indicating a side to be placed in contact with the patient or indicating a side to be placed not in contact with the patient. The tactile orientation indicators 360 may provide an intuitive indication to the patient of orientation, especially when used in a dark environment. The tactile orientation indicators 360 may be in the form of dots or other shapes. The tactile orientation indicators 360 may be used on the all of the headgear 314, or a portion thereof.

FIGS. 14-2 to 14-5 illustrate cross-sectional views of the straps having the tactile orientation indicators 360. As shown in FIGS. 14-4 and 14-5, the tactile orientation indicators may be in the form of a groove or recess. As shown in FIGS. 14-3 and 14-5, the tactile orientation indicators may be disposed on both side of the strap.

3.4 Keeping the Headgear in Place

The indicators 360 in FIG. 14-1 may also provide another function, to help maintain the headgear in place, e.g., by enhanced frictional/mechanical interface with the patient's head/hair.

FIGS. 14-6 to 14-11 illustrate examples of the present technology which might enable headgear to stay in place on the hair mechanically, whilst also not being too sticky or pulling on the hair. This can be achieved by selecting materials and/or structure to best manage the interface between hair and inner surface of headgear; and/or the interface between outer surface of headgear and pillow.

The rear headgear strap 715 shown in FIG. 14-6 may include piled or flocked textile (such as velvet ribbon) on the inner surface of the headband, which comes in direct contact with the hair and possibly the skin to create a non-slip effect. Additional effects of this surface might be a warmer or softer feel. FIG. 14-7 is a cross section along lines 14-7-14-7 of FIG. 14-6, and shows a padding layer 725, an outer fabric 730 and/or a velvet or velvet-like layer 735. The cross section is oval shaped to reduce sharp edges, but a more rectangular shape is possible also. Strap 715, in particular the flocked textile, includes a velvet pile 740, a fine warp 745, a weft 750 and a supplemental warp (velvet pile) 755.

When used as the inner fabric of a headgear strap, as best shown in FIG. 14-8 the fiber pile on the surface of the velvet ribbon functions to "comb" through the individual hairs 760 and therefore grips and prevents perpendicular movement across the hairs. It is not sticky, nor does it create a sensation of uncomfortable pulling. The velvet fibers function by gripping lightly, without pulling, via this combing effect.

The above materials/structure work best if stretch range characteristics similar to existing products on the market are maintained. Further, the existing headgear thickness range of foam/silicone/cushioning/foam alternatives, in addition to the thickness/length of the velvet pile (e.g., about +/−1-4 mm thick) should be held, but of course other alternatives are possible depending on the stiffness/thickness of the headgear.

In addition to having a functional inner surface for the headgear, a complimentary idea was that if the friction between the pillow and the headgear could also be reduced, then the headgear might drag less and stay in place better on the head, especially when the user was tossing and turning. Therefore, another example shown in FIGS. 14-9 to 14-11 includes a headgear 760 with an outer surface 765 including a more slippery or lower friction fabric, such as a satin, or including, or coated with, a low friction substrate, textile, metal, slippery silicone, laminate or other surface treatment. The inner surface 770 may have a flocking layer as described above, to comb through and hold onto hair strands 775. A middle layer 780 (e.g., of glue) may be used to hold the layers together. The strap may include tabs including hooks 785 to attach to loop portion formed on the outer surface 765 (opposite the flocking) of a hook and loop fastening arrangement.

3.5 Adjustment Indicators

Adjustment indicators may be included on the headgear. As illustrated in FIGS. 15-18, headgear strap 370 may include an end portion 373, which may include hook material, used to releasably connect to loop material on the headgear strap 370. Such a hook and loop material on the headgear may be used to connect portions of headgear to a mask or to other portions of headgear. For example, as illustrated in FIG. 11, end portion 373 of back of head portion 324 may include hook material adapted to connect to loop material on back of head portion 324 after being fed through slot 375. The end portion 373 may be pulled along and attached to the loop material to achieve a desired tightness of the back of head portion 324. The headgear may also be connected to the mask in such a fashion, with a slot formed in the mask through which an end portion of the headgear is fed, and pulled to a desired tightness, with the end portion connected to the loop material of the strap.

In FIG. 15, a series of adjustment indicators 372 are formed on strap 370. The adjustment indicators 372 may be a series of spaced elements adapted to provide the patient with feedback on how much the strap 370 has been tightened. The adjustment indicators 372 may be a series of protrusions or bumps. The patient or a user may count the number of adjustment indicators 372 that are pulled through slot 375. For example, in FIG. 11 two adjustment indicators have been pulled through slot 375. The patient can remember the number of adjustment indicators 372 pulled through the slot 375 and use this number when reapplying the headgear, thus removing the guesswork in tightening the headgear, and possibly preventing over-tightening. This can also reduce the time needed to adjust the headgear.

In addition, the protrusions or bumps can provide better retention of the headgear strap when the strap is under tension and provide easier attachment of the hook portion of the end portion 373 to the headgear strap since some of the load is taken up by the protrusion or bump of the adjustment indicators 372. The adjustment indicators 372 may be molded, heat welded or glued on to the strap 370 or may be a feature similar to a rivet passing through the headgear strap material. Additionally, the adjustment indicators 372 may be laminated to the headgear strap 370. The adjustment indicators 372 may be soft rubber, silicone, or a similar material. The adjustment indicators 372 may be clear or colored to match or contrast with the material of the headgear strap 372. The adjustment indicators 372 may be made of material that changes color with the amount of tension that is applied to it.

FIGS. 16-18 show variations of the adjustment indicators. In FIG. 16, adjustment indicators 374 vary in size, and may get progressively larger or progressively smaller. In FIG. 17, adjustment indicators 374 get progressively larger, and may be formed as partially circular, with one flat side 376. In FIG. 18, adjustment indicators 378 are formed as a series of spaced strips.

3.6. Length Adjustable Headgear

The headgear may include portions that are separable, to make it convenient for the patient or user to put on and take off the mask. For example, the headgear of FIGS. 7 through 14-1 includes adjustable connector 321 positioned on a top of the patient's head. It may also be beneficial to have the back of head strap 324 separable at the back of the patient's head.

Figure 19:
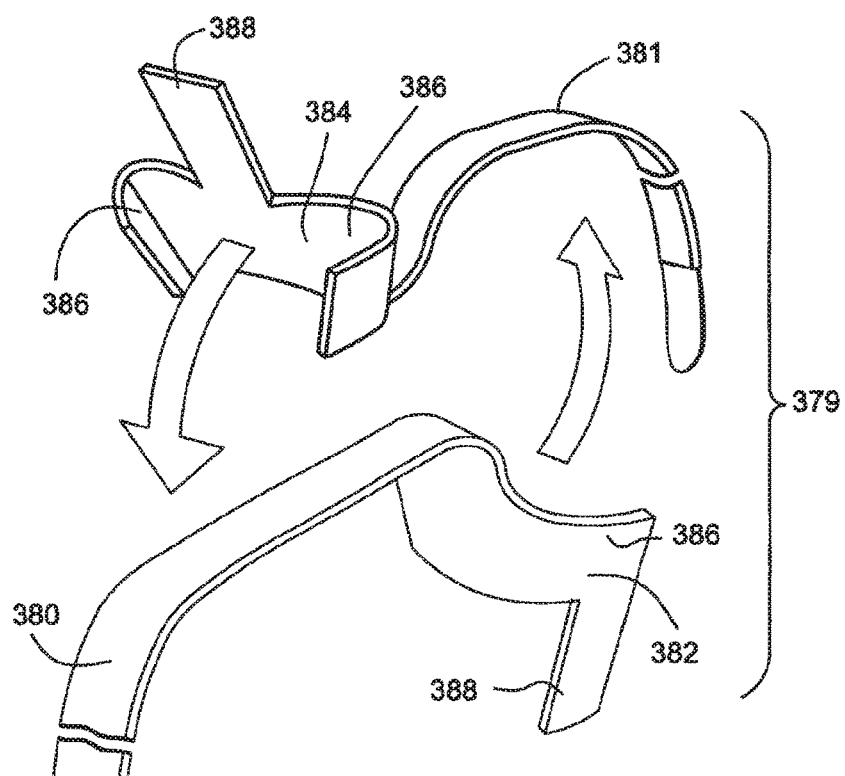
FIG. 19 is a perspective view of headgear straps with cuffs according to an embodiment of the present technology.
Figure 20:
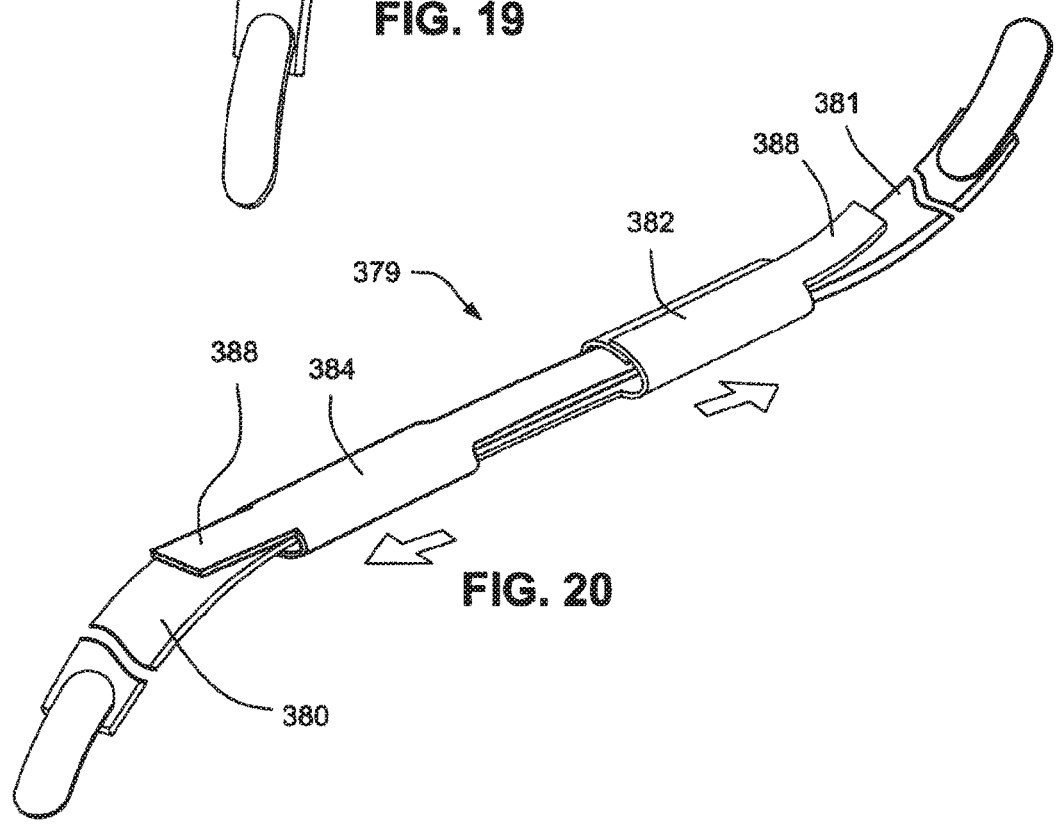
FIG. 20 is a perspective view of the headgear straps with cuffs of FIG. 19 in a closed position.

FIGS. 19 and 20 illustrate a strap 379, e.g., rear headgear strap, including a first headgear cuff 382 disposed at an end of first headgear strap 380 and a second headgear cuff 384 disposed at an end of the second headgear strap 381. The headgear cuffs 382 and 384 are adapted to releasably connect the headgear straps 380 and 381 to each other, in a length-adjustable manner. Each of the first headgear cuff 382 and the second headgear cuff 384 include one or more wing portions 386. The straps/cuffs each include at least one grip or tab portion 388. The wing portion 386 of the first cuff 382 is adapted to wrap around and/or connect to the second headgear strap 381 at a first position, and the wing portions 386 of the second cuff 384 are adapted to wrap around and/or connect to the first headgear strap 380 at a second position, longitudinally spaced from the first position. The wing portions 386 may connect to the headgear straps through the use of hook and loop material, (e.g., hook material of the wing portions and loop material on the straps). The tab portions 388 may hang loosely and are adapted to be pulled by the patient to release a respective one of the cuffs 382, 384 and/or to adjust the strap length/tension, e.g., by pulling the tabs in opposite directions.

The headgear cuffs 382, 384 may be used to adjustably connect any two portions of headgear and provide reliable connection and a quick release/adjustment by pulling on the tab portions. The headgear cuffs could be used in place of the adjustable connector 321 in FIG. 7, for example, to adjustably connect headgear 314.

FIGS. 20-1 to 20-6.3 show variants of an adjustable strap arrangement, using generally the same principal as exemplified in the examples of FIGS. 19-20. FIGS. 20-1 to 20-6.3 allow a patient or care provider to adjust the straps 380, 381 in an intuitive manner, e.g., by pulling them to tighten the straps, while ensuring that the strap ends are secured. For example, the ends of the straps are less likely to become tangled and thus present a neat and orderly appearance.

The straps shown in FIGS. 19 and 20-6.3 start from two straps which are threaded together to form the adjustable strap assembly.

For example, FIG. 20-1 includes a first strap 380 associated with a cuff 382, and a second strap 381 associated with a cuff 384. The cuffs can be made of a loop of material provided along or at the end of the respective straps, with each strap being threaded through the non-associated cuff, e.g., strap 380 extends through cuff 384.

FIGS. 20-2.1 to 20-2.5 show another arrangement where the assembly is shown in FIGS. 20-2.1, 20-2.4 and 20-2.5, and the individual straps 380, 381 and their respective cuffs 382, 384 are shown in FIGS. 20-2.2 and 20-2.3, respectively. In FIG. 20-2.1, the strap 381 extends under strap 380 from cuff 384 and is inserted into a slot 380s and through cuff 382 (FIGS. 20-2.4 and 20-2.5). Strap 380 is affixed to the cuff 382 and extends through cuff 384.

In the case of FIGS. 20-2.1 to 20-2.5, the cuffs are in the form of a metal casing forming a passage for the non-associated strap. The casing has ridges or dents 382.1, 384.1 on the side to enhance gripping. The metal casing cuffs may be overmoulded onto the straps using a side core.

FIGS. 20-3.1 and 20-3.2 illustrate another variant, similar to the one shown in FIGS. 20-2.1 to 20-2.6, with the strap 380 associated with cuff 382 passing under strap 381 and through cuff 384 (which is attached to strap 381).

FIG. 20-4 shows another variant, with cuff 384 being associated with strap 381 and cuff 382 associated with strap 380. Strap 380 extends above strap 381 and is inserted into a series of 2-3 slots in cuff 384, with strap 380 passing below the rear part of cuff 384 which includes a grip tab 384.2. Strap 381 passes below strap 380, and up through a first slot and then down into a second slot, passing under the rear part of cuff 382 and its grip tab 382.2.

FIG. 20-5 shows an example, similar to that of FIG. 20-4, but the cuffs and tabs are different. In particular, the strap 381 passes through a slot in the cuff 382, and then passes through a ring shaped tab 382.2. Likewise, the strap 380 passes through a pair of slots in cuff 384, and then through a ring-shaped tab 384.2.

FIGS. 20-6.1 to 20-6.3 show another variant, where FIGS. 20-6.2 and 20-6.3 show the straps 380, 381 in isolation and FIG. 20-6.1 shows the strap assembly. Strap 381 passes under strap 380, and then through a number (2-3) of slots in strap 380 and under a rear part of the cuff 382 including a U-shaped tab 382.2. Strap 380 passes over strap 381, through a series of slots (e.g., 2-3) in cuff 384, and under a rear part of cuff 384 having the tab 384.2.

As shown in various ones of FIGS. 20-2.1 to 20-6.3, one or both of the headgear straps 380, 381 may include one or more locking bumps 381.1 (molded, attached and/or formed). In an example, the bumps, e.g., resilient and elastically deformable material, may be cast onto a textile, followed by a "weld cut" to form edge and shape, e.g., to have a curved edge as shown in FIG. 14-7. "Weld cut" refers to ultrasonic welding in this context. The bumps (having a thickness of 0.1 to 3 mm and a height that is equal to or less than the height of the strap) may aid the patients in re-tightening the headgear to the desired setting (e.g., the bumps could be numbered), and/or the bumps may enhance or become the tentative feature to ensure the headgear remains in its set position. The straps can have a variety of different constructions and/or materials, e.g., soft fabrics (FIG. 20-1), laminated foams, non-stretched materials, plastic overmoulds (FIGS. 20-4 to 20-6.3) and/or textile surface casting.

Further, the grip tabs may be molded, attached or formed. For example, the strap end may have a grip tab, e.g., formed of a grippable material (e.g., polymer (silicone or polyurethane)), as shown in FIGS. 20-4 to 20-6.3. In the case FIG. 20-6, only the upper or exposed strap (FIG. 20-6.2) includes locking bumps, whereas each end of each strap (FIGS. 20-6.2 to 20-6.3) includes locking bumps.

3.7 Alternative Headgear Adjustment

Figure 23:
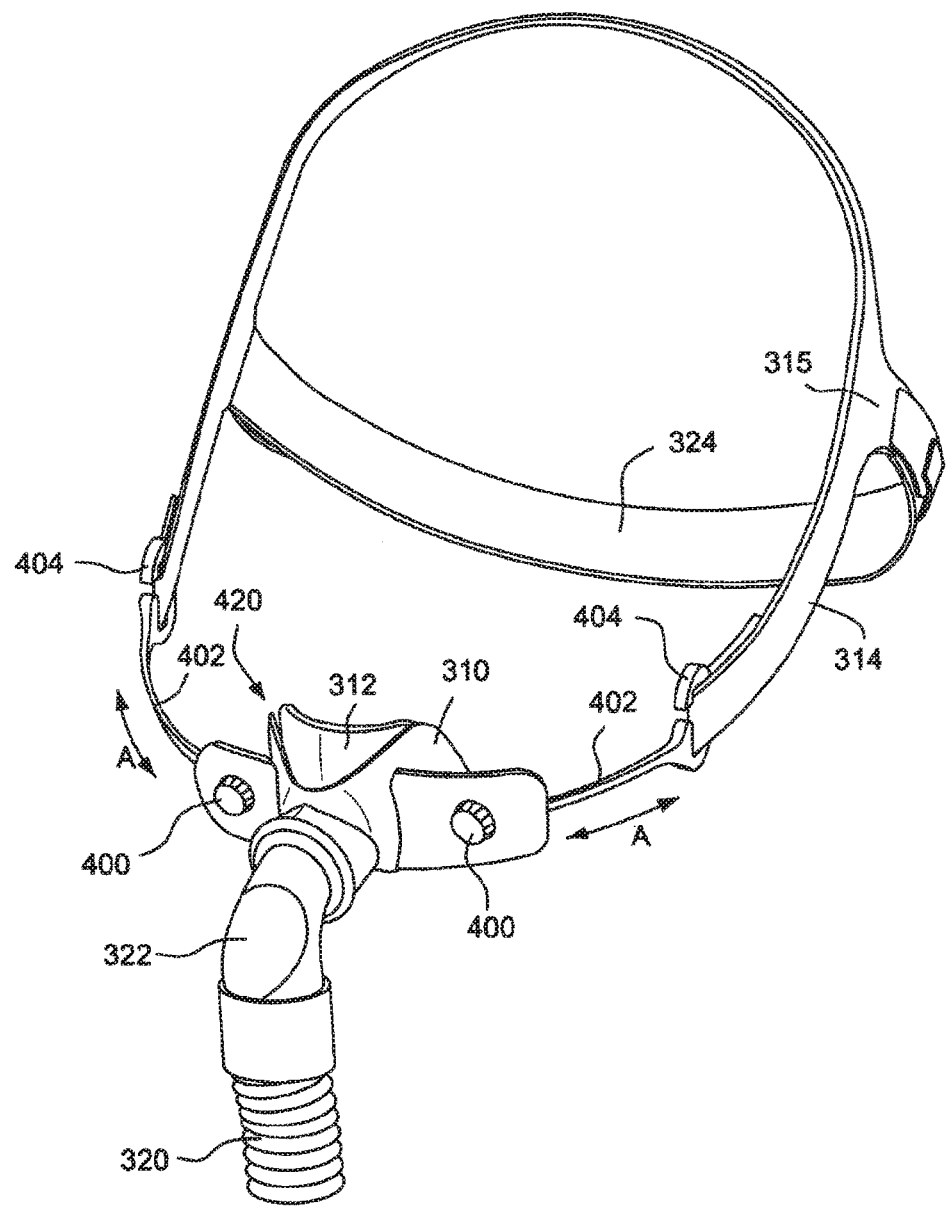
FIG. 23 is a perspective view of a patient interface with headgear adjustment dials according to an embodiment of the present technology.
Figure 24:
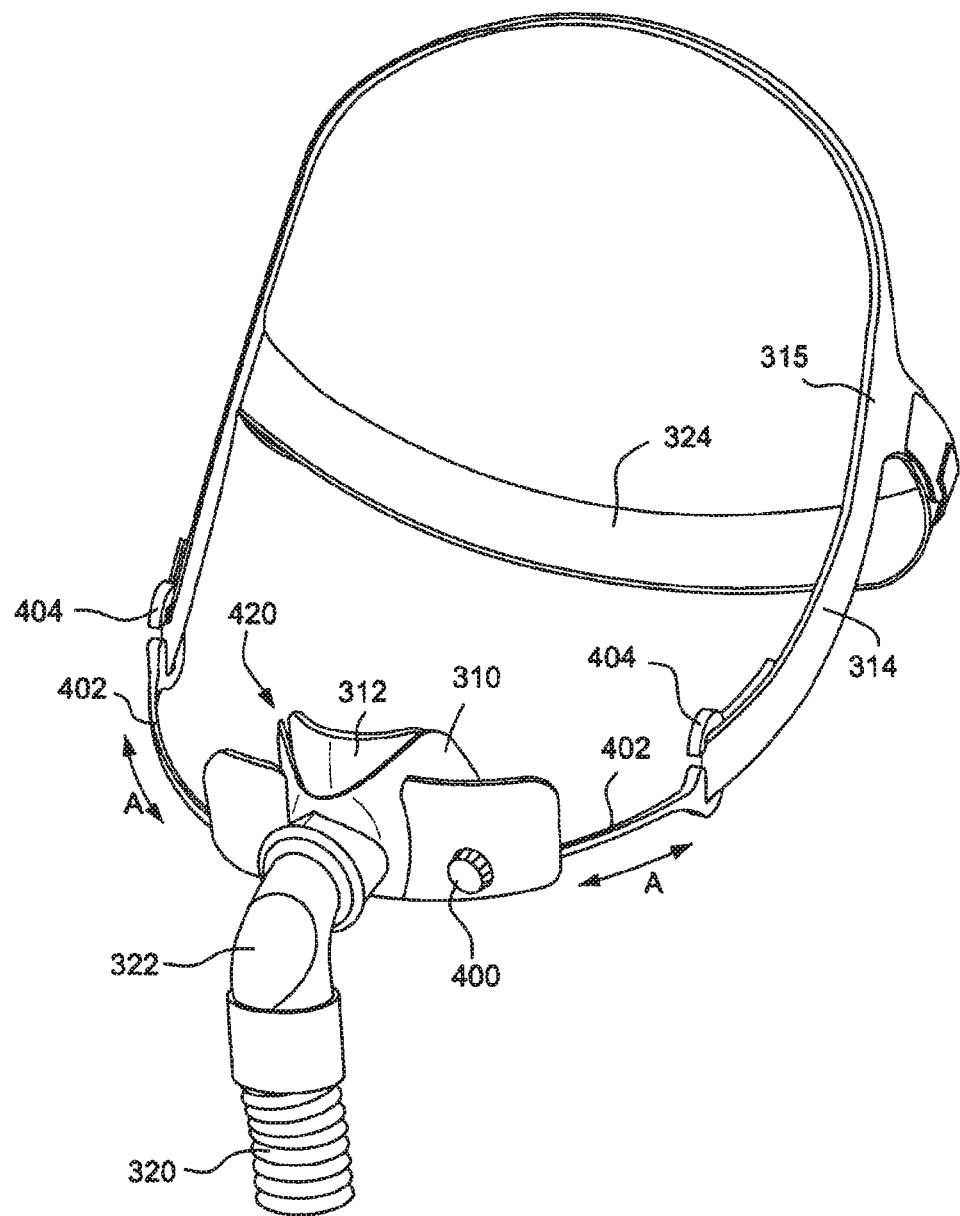
FIG. 24 is a perspective view of a patient interface with a headgear adjustment dial according to an embodiment of the present technology.

FIGS. 23 and 24 illustrate patient interfaces 300 having alternative headgear adjustment. The patient interfaces 420 include chords 402 connected to masks 310. The chords 402 each have a connector with an aperture or slot 404 adapted to connect to headgear 314. The chords 402 may be moved in the directions of arrows A to either tighten or loosen the headgear. In FIG. 23, each chord is connected to an adjustment device 400, e.g., a dial, on the mask 310. The adjustment devices 400 each have a pinion or winder wheel that winds the chord in or out when the dials are turned. In the embodiment of FIG. 24, only one adjustment device 400 is used, with both cords 402 connected to the adjustment device 400. When the adjustment device of FIG. 24 is turned, both chords 402 wind in or out to tighten or loosen the headgear. As an alternative to the chord 402, two parallel cords forming a rack could be used on each side of the mask 310.

Figure 25:
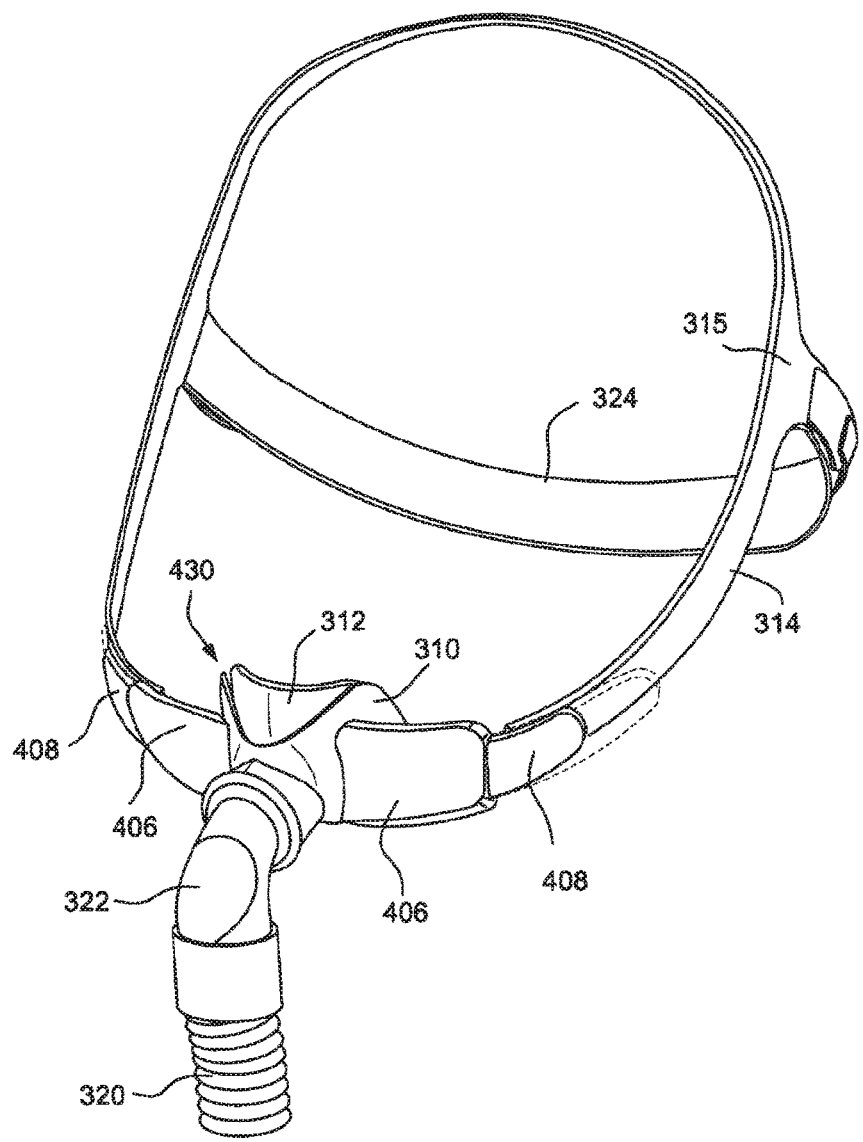
FIG. 25 is a perspective view of a patient interface with headgear adjustment clips according to an embodiment of the present technology.

FIG. 25 illustrates a patient interface 430 having alternative headgear adjustment. The patient interface 430 includes a mask 310 having first and second side portions 406 and first and second headgear clips 408. The headgear clips 408 connect to headgear 314 by the use of hook and loop material or by other connection means. The headgear clip 408 is moveable to different positions within apertures formed in the side portions, for example by pulling or pushing on the headgear clip 408, to selectively tighten or loosen the headgear 314. The headgear clips may lock into the positions, and be moveable to a new position when sufficient force is applied to the clips 408. The first and second headgear clips 408 are moveable between the plurality of positions by application of a predetermined force.

3.8 Tiltable Mask

Figures 1, 26:
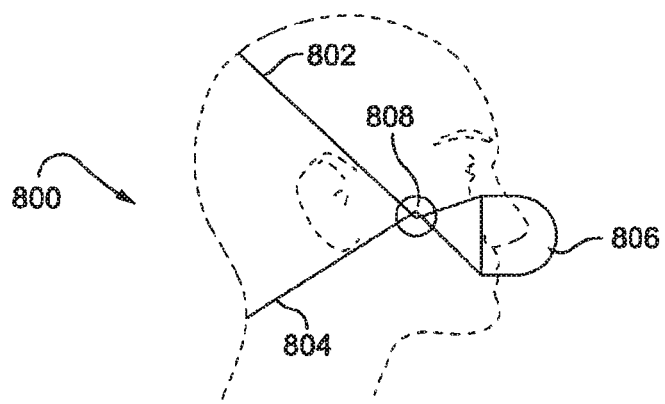
Figures 2, 26:
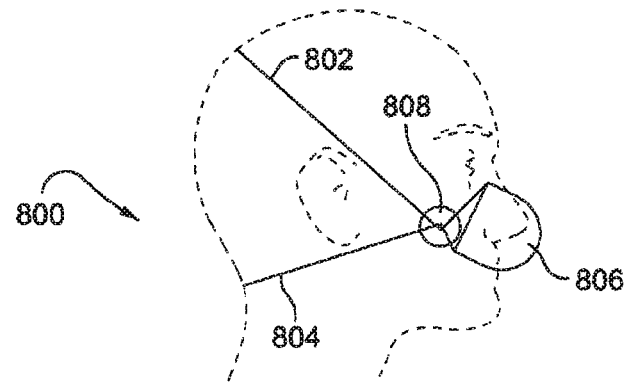
Figures 3, 26:
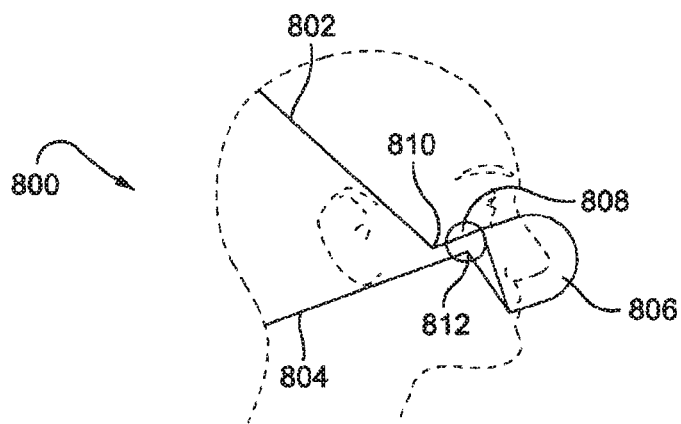
Figures 4, 26:
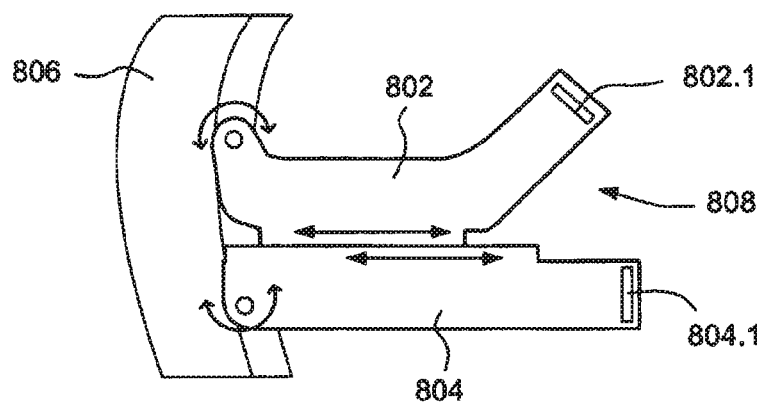
Figures 5, 26:
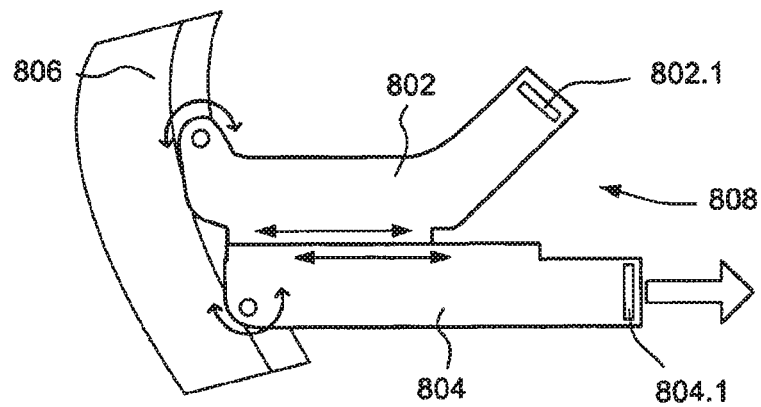
Figures 6, 26:
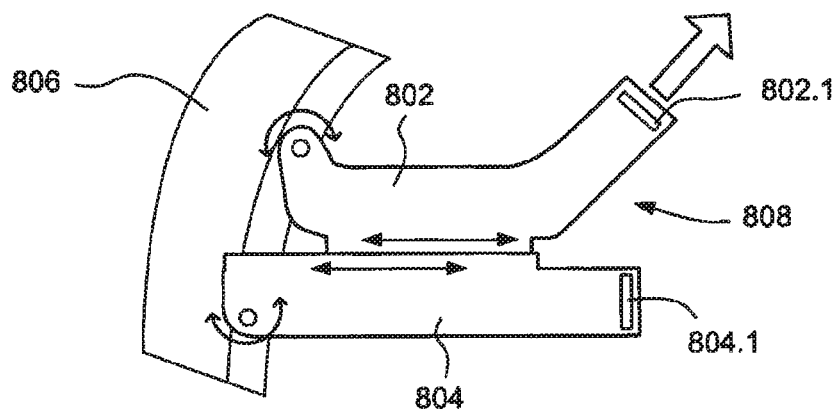

As shown in FIGS. 26-1 to 26-3, a headgear assembly 800 may include a first or top strap 802 and a second or bottom strap 804, each of which may be connected to a mask 806. The headgear assembly may also include an adjustment device 808. In operation, the top strap may slide relative to the bottom strap 804, and vice versa, and the top and/or bottom straps may move relative to the adjustment device 808, and vice versa. This may in effect tilt or angle of the mask away from the nose bridge (FIG. 26-2), or away from the chin region (full face mask) or top lip region (nasal mask)—per FIG. 26-3. FIG. 26-1 shows the situation where the mask is oriented in a generally horizontal position. When viewed from the side, each of the top strap and bottom strap is in a substantially V-shape and/or converge towards each other to meet at the adjustment device 808, in this example, a slider. The slider may wind, push or otherwise move the apex 810 of the V-shape of the top strap forwards (closer to the mask) while moving the apex 812 of the V-shape of the bottom strap (away from the mask) so as to tilt the mask away from the patient's nose bridge (see FIG. 26-2), while the opposite is happening in the (FIG. 26-3). In addition, both of the top and bottom straps can be moved relative to the slider to locate the position of the slider in a front to back direction in order to position the slider on the most optimum position relative to the patient, e.g., to maintain proper headgear vectors for the given patient's physiology and mask type, and/or to position the slider in the least obtrusive and/or most comfortable position (out of the patient's line of sight), etc., while maintaining proper sealing, reducing potential for movement, etc. This arrangement can help avoid the need for a forehead support (thus improving line of sight and allowing the patient to wear glasses) while at the same time having the ability to redistribute forces from the nasal bridge region to the upper lip region or the chin region, or vice versa, although of course an adjustable forehead support could also be used for this reason.

FIGS. 26-4 to 26-6 illustrate a more specific example of the adjustment device 808 shown in FIGS. 26-1 to 26-3. FIG. 26-4 shows a mask 806 with upper and lower vector members or straps 802, 804 attached thereto. Each vector member 802, 804 includes a slotted connected 802.1, 804.1 at one end to connect with upper and lower straps, respectively. The other end of the vector member is connected (e.g., pivotably) to the mask 806, e.g., the mask frame. The vector members cooperate with one another and the mask to allow fitting of the mask. For example, the vector members may be slidable relative to one another along a track, e.g., a tongue and groove arrangement or a roller and track arrangement. The vector members can be extensions of or a part of the headgear and/or the headgear straps may have rigidizers or stiffeners to enable easier and more reliable sliding. Sliding may occur proximate the patient's cheek region. Alternatively, sliding may occur near the jaw or mouth region.

FIG. 26-4 shows the neutral position, which FIGS. 26-5 and 26-6 show tilted positions of the mask. In FIG. 26-5, pulling the bottom strap 804 tilts base of mask into chin, while pulling the top strap 802 tilts nose portion of the mask back towards the nasal bridge region.

In an alternative, the vector members or straps need not be attached to one another. For example, they could pivot at the mask/frame, so that forces actually rotate the mask/frame and pull backwards, rather than just translate the mask in that vector's direction.

3.9 Adjustable Forehead Support

Figures 1, 27:
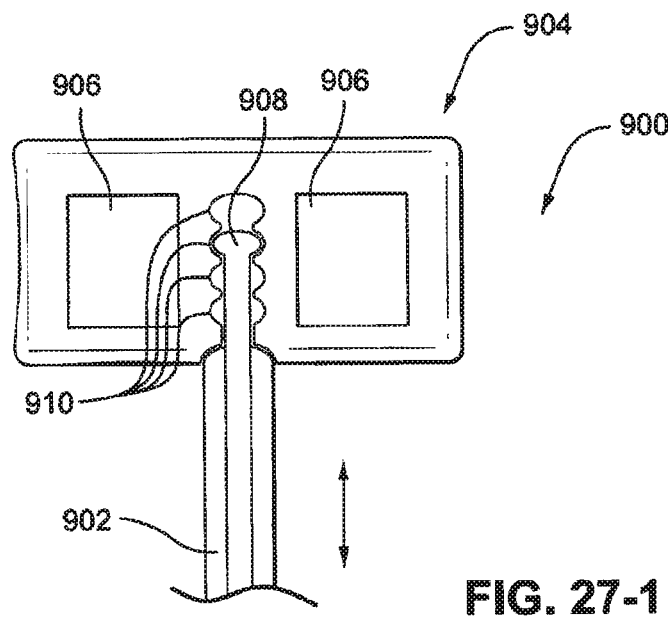
Figures 2, 27:
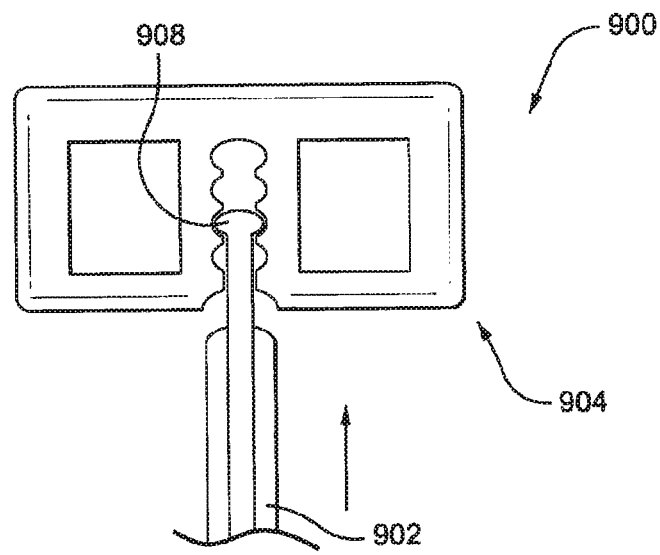

FIGS. 27-1 and 27-2 show an example of an adjustable forehead support 900. In this example, a mask frame includes a joining portion 902 which might be formed as part of or otherwise coupled or connected to the mask frame. The remainder of the mask frame is not shown, but would typically also support the mask cushion, and possibly other componentry.

The adjustable forehead support may include a headgear connector 904 adapted to support one or more forehead cushions (e.g., of elastic and/or foam), or headgear straps themselves can form padding between the headgear connector and the patient's forehead, e.g. by threading the headgear straps through apertures 906 and doubling each headgear strap back over itself using a hook and loop fastener.

Headgear connector 904 may be slidably adjustable with a mask frame, e.g., in a generally vertical, linear motion, as indicated by the double headed arrows. FIG. 27-1 shows the cushion frame in its lower position, while FIG. 27-2 shows the cushion frame in one of its raised positions. There may be from 2-10 positions (four are shown in the example).

The headgear connector 904 may be made from a flexible, resilient material. The joining portion 902 of the frame may include one or more nodules 908 and the headgear connector may include from 2-10 recesses (again 4 are shown) adapted receive the one or more nodules of the frame. This arrangement is suitable to anchor the headgear connector in position, but if enough force is applied (preferably in a direction different to the headgear tension) the headgear connector (e.g., the relevant recess(es) thereof) may flex to pass the nodule(s) it is anchored on and stop at the next nodule/recess. This allows a height or lengthwise adjustment of the position of the headgear connector.

It should be noted that the headgear connector in FIGS. 27-1 and 27-2 is in the form of a forehead support. However, headgear connectors and/or the headgear which are provided on the lateral sides of the mask could also include such an arrangement.

3.10 Alternative Headgear Materials

The headgear may be formed from alternative materials that are breathable, stretchable, formable and a durable fabric, while being cost effective and easily manufactured. The alternative materials may be one or more of the following: spacer fabric, polymers such as thermoplastic elastomer or polypropylene, microfiber, chamois, suede, leather, vinyl, bamboo, perforated neoprene, elastic webbing, nylon webbing, mesh, cotton, Lycra, a thick or layered fabric with no foam, a high density foam in a composite, a knitted fabric including tailored knitting, a compression garment fabric, wool including merino wool, GoreTex, (i.e., light weight, strong and breathable fabric that may have wicking properties), alternative loop materials to UBL including Velstretch™, viscoelastic foam, memory foam, expanded foam, Teflon, woven Kevlar, Nitinol (memory metals), Nitinol and fabric composites, and/or a fabric tube with a filling (e.g., like a bean bag). The fabric tube with a filling may have a filling that is re-heat bale such that the filling could be heated by the patient, (e.g., place headgear in a microwave) and could have a scented inner material (e.g., having lavender scent).

3.11 Alternative Headgear Manufacturing Methods

The headgear may have manufactured by various methods. Any of the following methods may be used, for example: glue laminating layers of material together, plasma lamination, film lamination, ultrasonically weld composite materials together, heat weld layers of material together, stitching or sewing layers of material together, molded foam (skinned or unskinned), die cut or compression cut foam, foam with a coating on its outer surface (e.g., spray coating), material knitted into in use shape of headgear, tailored knitting whereby multiple sections of fabric are knitted together, molding polymer onto fabric outer layer by placing fabric in the mold and then injecting or compressing polymer onto the fabric layer, multiple layers of fabric formed together with no foam, laminating foam and Teflon with Teflon contacting the patient's skin to reduce friction with the patient's skin, and laminating silicone and Teflon.

Figure 21:
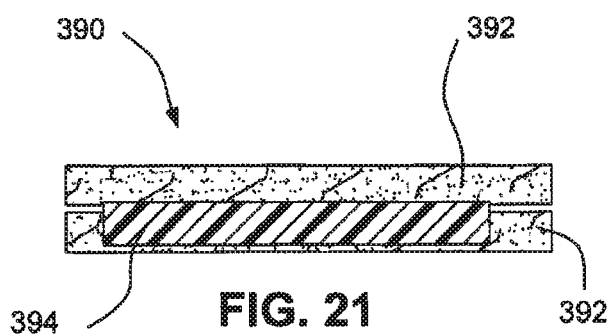
FIG. 21 is a side view of a headgear formation process according to an embodiment of the present technology.

Additionally, as illustrated in FIG. 21, a headgear material 390 may be formed by extruding a layer of polymer 394, such as a thermoplastic elastomer, and as the polymer 394 is being extruded, fabric 392 is laminated onto the polymer 394.

Figure 22:
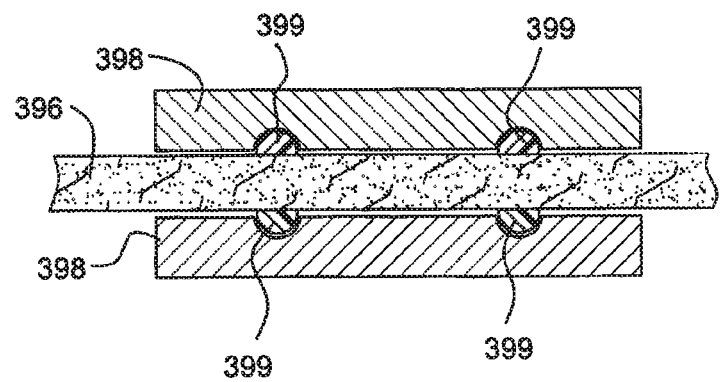
FIG. 22 is a side view of a headgear formation process according to an embodiment of the present technology.
Figures 1, 22:
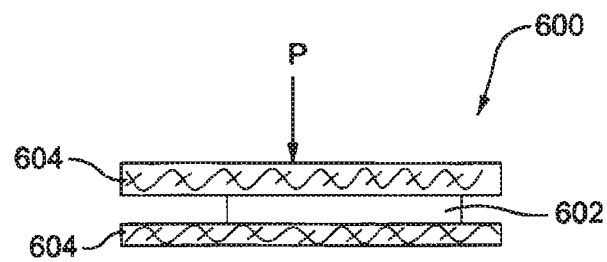
Figures 2, 22:
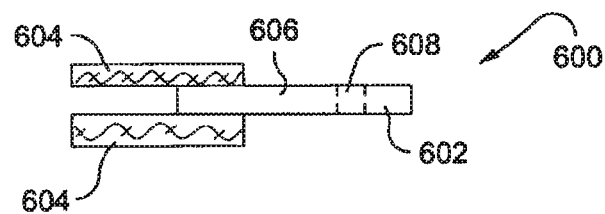
Figures 3, 22:
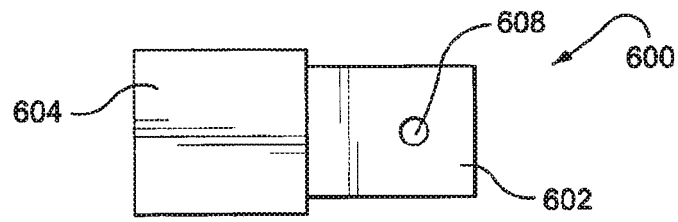
Figures 4, 22:
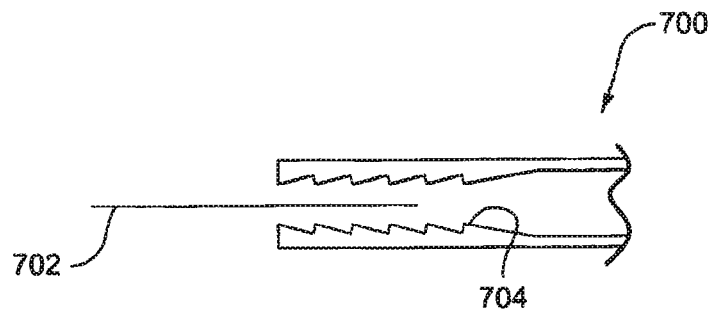

As illustrated in FIG. 22, a fabric layer 396 may be inserted in a tool 398 may be utilized, with foam 399 or another material injected into gaps in the tool when the tool is closed. This method may be used to form the adjustment indicators 372 on the headgear strap 370, as illustrated in FIG. 15, for example.

3.12 Exposed Rigidizer

FIGS. 22-1 to 22-3 show a composite material headgear strap 600 including a rigidizer 602 and a fabric portion 604, e.g., including a portion positioned on each face of the rigidizer. The headgear strap may be made by thermoforming the rigidizer within the fabric portion (for example, place fabric sheets on each side of the rigidizer and then thermoform), then cut, e.g., die cut, the composite material. When die cutting the composite material, the fabric may be cut away from the rigidizer (e.g., at the position P) so that one or more portions 606 of the rigidizer may be exposed. These exposed portions of the rigidizer may be utilized for connecting to the mask, for example.

The exposed rigidizer may also be cut when the fabric is cut (or after), for example one or more holes 608 may be cut for engagement with the mask.

The rigidizer may also have foam or other conformable materials with it inside the fabric outer layer.

3.13 Exposed Polymer

In a variant, a headgear strap made of a polymer may be molded onto a fabric, forming a composite strap. In one example, the fabric may extend along a portion of the strap, so that a portion of the strap is the composite and another portion of the strap is polymer. This may be useful, for example, if the fabric is positioned to contact sensitive areas of the patient's face such as the cheek, and the polymer portion was positioned to connect with other parts of the mask system for example another headgear strap or the patient interface.

3.14 Metal Rigidizers

Metal can be an ideal rigidizer because most metals are inextensible. FIG. 22-4 shows a metal rigidizer 700 that may be adhesively attached to a headgear strap 702. Alternatively, the metal may be molded on to the strap 702, for example, the metal may first be formed in the desired shape, then a thermoplastic may be overmolded on to the metal, then this composite may be attached, e.g., using heat or ultrasonic welding on to a conformable material such as a fabric.

The metal rigidizer may be mechanically attached. For example, a strap made of fabric or other conformable material may be clamped between metal teeth 704—see FIG. 22-4. The metal portion may be a stiffener attached to the mask or other part of the headgear.

The metal rigidizer may be formed with a polymer outer in a continuous extrusion. A portion of the metal inner layer may then be exposed by stripping off the polymer to expose the metal inner. The metal may then be utilized to connect the rigidizer to the patient interface or other part of the mask system. Alternative—instead of a polymer extrusion, foam could be foamed onto the outside of the metal. Further alternative, fibers or fabric could be flocked or otherwise formed with the metal inner—for example an arrangement similar to pipe cleaners.

Metal may also be malleable so the patient can adapt the shape of the headgear to suit them. Since metals may be stiffer than polymers currently used in rigidizers, the rigidizer may be smaller when formed from metal.

The surface of the metal could be treated for example anodized, powder coated, dip coated, zinc coated, chrome coated, blasted etc to create an aesthetically appealing surface finish.

4. Additional Embodiments

It is believed that a patient interface in accordance with the present technology is more able to accommodate different sizes and shapes of faces and noses than prior designs. It is believed that a patient interface in accordance with the present technology may reduce the need for inventory in different sizes. It is believed that a patient interface in accordance with the present technology can provide improved comfort for patents, and improved compliance with their therapy.

While the technology has been described in connection with what are presently considered to be the most practical and preferred embodiments, it is to be understood that the technology is not to be limited to the disclosed embodiments, but on the contrary, is intended to cover various modifications and equivalent arrangements included within the spirit and scope of the technology. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the technology has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A patient interface for delivering breathable gas to a patient, the patient interface comprising:
    a mask having a sealing portion adapted to form a seal with the patient, the mask having headgear connectors;
    headgear adapted to secure the mask to a head of the patient, the headgear having a first strap portion and a second strap portion, the first strap portion adapted to connect to the mask, the second strap portion adapted to connect to and be separable from the first strap portion;
    a first alignment indicator disposed on the mask;
    a second alignment indicator disposed on the first strap portion; and
    a third alignment indicator disposed on the second strap portion,
    wherein the first and second alignment indicators are positioned to align with each other when the first strap portion is connected to the mask with a correct alignment, and the second and third alignment indicators are positioned to align with each other when the first strap portion is connected to the second strap portion with a correct alignment.

2. A patient interface according to claim 1, wherein the first alignment indicator, the second alignment indicator and the third alignment indicator are in the form of lines.

3. A patient interface according to claim 1, wherein the first alignment indicator, the second alignment indicator and the third alignment indicator have a common texture and/or color.

4. A patient interface according to claim 3, wherein the common texture or color contrasts with a texture or color of the mask, the first strap portion and/or the second strap portion.

5. A patient interface according to claim 1, wherein the second alignment indicator extends on the first strap portion between where the first strap portion connects to the mask and where the first strap portion connects to the second strap portion.

6. A patient interface according to claim 1, wherein the second strap portion connects at opposite ends to two different portions of the first strap portion.

7. A patient interface according to claim 6, wherein the third alignment indicator extends between the opposite ends of the second strap portion.

8. A patient interface according to claim 1, wherein the second strap portion is a back of head strap portion adapted to wrap around a back of the patient's head in use.

9. A patient interface according to claim 1, wherein the headgear includes a pair of headgear connectors disposed on opposite sides of the mask, the first strap portion having a first end connected to a first one of the headgear connectors and a second end connected to a second one of the headgear connectors, wherein the first alignment indicator is disposed on both sides of the mask.

10. A patient interface according to claim 1, wherein the headgear includes a pair of headgear connectors disposed on opposite sides of the mask, the first strap portion having a first end connected to a first one of the headgear connectors and a second end connected to a second one of the headgear connectors, wherein the first alignment indicator is disposed on only one of the sides of the mask.

11. A patient interface according to claim 1, further comprising an orientation indicator provided on the mask.

12. A patient interface according to claim 11, wherein the orientation indicator is a shape of the sealing portion.

13. A patient interface according to claim 1, further comprising an orientation indicator provided on the headgear.

14. A patient interface according to claim 13, wherein the orientation indicator is printing provided on the headgear.

15. A patient interface according to claim 13, wherein the orientation indicator is an embossed orientation indicator.

16. A patient interface according to claim 13, wherein the orientation indicator is a line on the headgear.

17. A patient interface according to claim 16, wherein the orientation indicator is provided on a side of the headgear to indicate a front side or a back side.

18. A patient interface according to claim 13, wherein the orientation indicator is a tactile orientation indicator.

19. A patient interface according to claim 18, wherein the tactile orientation indicator is a plurality of raised or indented elements that provide tactile feedback to the patient.

20. A patient interface according to claim 1, wherein the first and second alignment indicators are positioned to be misaligned with each other when the first strap portion is connected to the mask with an incorrect alignment.

21. A patient interface according to claim 1, wherein the second and third alignment indicators are positioned to be misaligned with each other when the first strap portion is connected to the second strap portion with an incorrect alignment.

22. A patient interface according to claim 1, wherein the first and second alignment indicators are configured to be adjacent to each other only when the mask is positioned in a particular orientation relative to the first strap portion.

* * * * *